United States Patent
DeLuca et al.

(10) Patent No.: US 6,835,723 B2
(45) Date of Patent: Dec. 28, 2004

(54) 2-METHYLENE-19-NOR-20(S)-1α-HYDROXY-BIS-HOMO-PREGNACALCIFEROL IN CRYSTALLINE FORM

(75) Inventors: Hector F. DeLuca, Deerfield, WI (US); James B. Thoden, Madison, WI (US); Hazel M. Holden, Fitchburg, WI (US); Margaret Clagett-Dame, Deerfield, WI (US); Sumithra Gowlugari, Madison, WI (US); Pawel Grzywacz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 131 days.

(21) Appl. No.: 10/317,467

(22) Filed: Dec. 12, 2002

(65) Prior Publication Data

US 2003/0204103 A1 Oct. 30, 2003

Related U.S. Application Data

(60) Provisional application No. 60/341,138, filed on Dec. 13, 2001.

(51) Int. Cl.[7] .................. A61K 31/59; C07C 401/00
(52) U.S. Cl. ......................................... 514/167; 552/653
(58) Field of Search ........................... 514/167; 552/653

(56) References Cited

U.S. PATENT DOCUMENTS 5,936,133 A * 8/1999 DeLuca et al. ............. 568/828

* cited by examiner

*Primary Examiner*—Alton N. Pryor
(74) *Attorney, Agent, or Firm*—Andrus, Sceales, Starke & Sawall, LLP

(57) ABSTRACT

A method of purifying 2-methylene-19-nor-20(S)-1α-hydroxy-bis-homo-pregnacaciferol to obtain 2-methylene-19-nor-20(S)-1α-hydroxy-bis-homo-pregnacalciferol in crystalline form. The method includes the steps of boiling a solvent such as acetone under inert atmosphere, dissolving a product containing 2-methylene-19-nor-20(S)-1α-hydroxy-bis-homo-pregnacalciferol to be purified in the solvent, cooling the solvent and dissolved product below ambient temperature for a sufficient amount of time to form a precipitate of 2-methylene-19-nor-20(S)-1α-hydroxy-bis-homo-pregnacalciferol crystals, and recovering the 2-methylene-19-nor-20(S)-1α-hydroxy-bis-homo-pregnacalciferol crystals.

9 Claims, 1 Drawing Sheet

2-METHYLENE-19-NOR-20(S)-1α-HYDROXY-BIS-HOMO-PREGNACALCIFEROL IN CRYSTALLINE FORM

CROSS REFERENCE TO RELATED APPLICATIONS

This application is based on and claims priority from U.S. Provisional Patent Application No. 60/341,138 filed Dec. 13, 2001.

BACKGROUND OF THE INVENTION

The present invention relates to purification of organic compounds, and more particularly to the purification of 2-methylene-19-nor-20(S)-1α-hydroxy-bis-homo-pregnacalciferol (referred to herein as 2MBP and/or 2-MbisP) by preparing it in crystalline form.

Purification of organic compounds, especially those designated for pharmaceutical use, is of considerable importance for chemists synthesizing such compounds. Preparation of the compound usually requires many synthetic steps and, therefore, the final product can be contaminated not only with side-products derived from the last synthetic step of the procedure but also with compounds that were formed in previous steps. Even chromatographic purification, which is a very efficient but relatively time-consuming process, does not usually provide compounds which are sufficiently pure to be used as drugs.

Depending on the method used to synthesize 1α-hydroxyvitamin D compounds, different minor undesirable compounds can accompany the final product. Thus, for example, if direct C-1 hydroxylation of 5,6-trans geometric isomer of vitamin D is performed, followed by $SeO_2$/NMO oxidation and photochemical irradiation [see Andrews et al., *J. Org. Chem.* 51, 1635 (1986); Calverley et al., *Tetrahedron* 43, 4609 (1987); Choudry et al., *J. Org. Chem.* 58, 1496 (1993)], the final 1α-hydroxyvitamin D product can be contaminated with 1β-hydroxy- as well as 5,6-trans isomers. If the method consists of C-1 allylic oxidation of the 4-phenyl-1,2,4-triazoline-3,5-dione adduct of the previtamin D compound, followed by cycloreversion of the modified adduct under basic conditions [Nevinckx et al., *Tetrahedron* 47, 9419 (1991); Vanmaele et al., *Tetrahedron* 41, 141 (1985) and 40, 1179 (1991); Vanmaele et al., *Tetrahedron Lett.* 23, 995 (1982)], one can expect that the desired 1α-hydroxyvitamin can be contaminated with the previtamin 5(10),6,8-triene and 1β-hydroxy isomer. One of the most useful C-1 hydroxylation methods, of very broad scope and numerous applications, is the experimentally simple procedure elaborated by Paaren et al. [see *J. Org. Chem.* 45, 3253 (1980) and *Proc. Natl. Acad. Sci. U.S.A.* 75, 2080 (1978)]. This method consists of allylic oxidation of 3,5-cyclovitamin D derivatives, readily obtained from the buffered solvolysis of vitamin D tosylates, with $SeO_2$/t-BuOOH and subsequent acid-catalyzed cycloreversion to the desired 1α-hydroxy compounds. Taking into account this synthetic path it is reasonable to assume that the final product can be contaminated with 1α-hydroxy epimer, 5,6-trans isomer and the previtamin D form. 1α-hydroxyvitamin $D_4$ is another undesirable contaminant found in 1α-hydroxyvitamin D compounds synthesized from vitamin $D_2$ or from ergosterol. 1α-hydroxyvitamin $D_4$ results from C-1 oxidation of vitamin $D_4$, which in turn is derived from contamination of the commercial ergosterol material. Typically, the final product may contain up to about 1.5% by weight 1α-hydroxyvitamin $D_4$. Thus, a purification technique that would eliminate or substantially reduce the amount of 1α-hydroxyvitamin $D_4$ in the final product to less than about 01.–0.2% would be highly desirable.

The vitamin D conjugated triene system is not only heat- and light-sensitive but it is also prone to oxidation, leading to the complex mixture of very polar compounds. Oxidation usually happens when a vitamin D compound has been stored for a prolonged time. Other types of processes that can lead to a partial decomposition of vitamin D compounds consist of the some water-elimination reactions; their driving force is allylic (1α-) and homoallylic (3β-) position of the hydroxy groups. The presence of such above-mentioned oxidation and elimination products can be easily detected by thin-layer chromatography. Thus, for example, using precoated aluminum silica sheets [with UV indicator; from EM Science (Cherry Hill, N.J.)] and solvent system hexane-ethyl acetate (4:6), the spot of 1α-OH-$D_2$ ($R_f$ 0.27) and its elimination products ($R_f$'s ca. 0.7–0.9) are visible in ultraviolet light. Also, after spraying with sulfuric acid and heating, an additional spot can be visualized ($R_f$ 0), derived from oxidation products.

Usually, all 1α-hydroxylation procedures require at least one chromatographic purification. However, even chromatographically purified 1α-hydroxyvitamin D compounds, although showing consistent spectroscopic data, suggesting homogeneity, does not meet the purity criteria required for therapeutic agents that can be orally, parenterally or transdermally administered. Therefore, it was evident that a suitable method of purification of 2MBP is required.

SUMMARY OF THE INVENTION

The present invention relates to a method of purifying 2MBP by means of crystallization to obtain 2MBP in crystalline form. The solvent plays a crucial role in the crystallization process, and is typically an individual liquid substance or a suitable mixture of different liquids. For crystallizing 2MBP, the most appropriate solvent and/or solvent system is characterized by the following factors:

(1) low toxicity;

(2) low boiling point;

(3) significant dependence of solubility properties with regard to temperature (condition necessary for providing satisfactory crystallization yield); and (4) relatively low cost.

It was found that highly apolar solvents (e.g. hydrocarbons) were not suitable due to the low solubility of 2MBP in them. Quite the reverse situation occurred in highly polar solvent media (e.g. alcohols), in which 2MBP showed too high solubility. Therefore, it was concluded that for the successful crystallization of 2MBP, a solvent of medium polarity is required. Interestingly, hexane, so frequently used for crystallization purposes, was found less suitable for crystallization of 2MBP. However, it was found that an individual solvent, namely acetone, was most useful for the crystallization of 2MBP. In addition, it is believed that solvent systems utilizing ethyl acetate, or isopropanol, or chloroform, or dichloromethane, or diethyl ether would also perform well. These solvents are all very easy to remove by evaporation or other well known methods. In all cases the crystallization process occurred easily and efficiently; and the precipitated crystals were sufficiently large to assure their recovery by filtration.

DETAILED DESCRIPTION OF THE INVENTION

Figure 1:
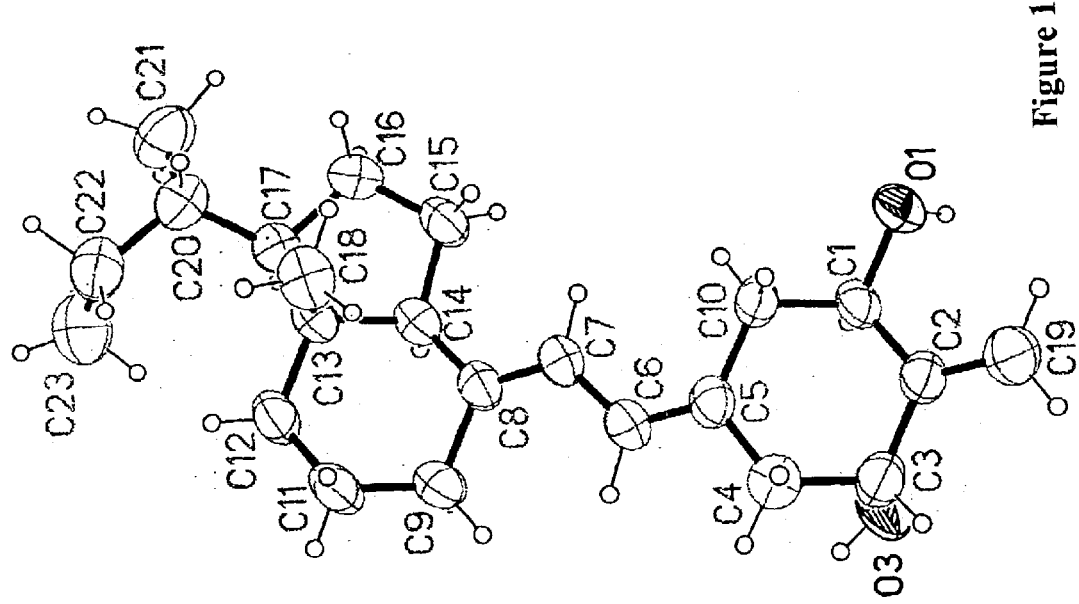
FIG. 1 is an illustration of the three dimensional structure of 2MBD as defined by the atomic positional parameters discovered and set forth herein.

The present invention provides 2-methylene-19-nor-20 (S)-1α-hydroxy-bis-homo-pregnacalciferol (2MBP) in crystalline form, a pharmacologically important compound, characterized by the formula shown below:

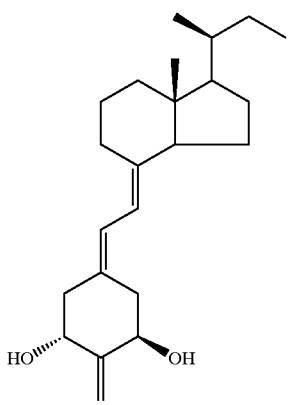

I

The present invention also provides a valuable method of purification of 2MBP. The purification technique involves obtaining the 2MBP product in crystalline form by utilizing a crystallization procedure wherein the 2MBP material to be purified is dissolved using as the solvent a single solvent system comprised of acetone, ethyl acetate, isopropanol, chloroform, dichloromethane, or diethyl ether. The preferred solvent is acetone. Thereafter, the solvent can be removed by evaporation, with or without vacuum, or other means as is well known. The technique can be used to purify a wide range of final products containing 2MBP obtained from any known synthesis thereof, and in varying concentrations, i.e. from microgram amounts to kilogram amounts. As is well known to those skilled in this art, the amount of solvent utilized should be minimized and/or adjusted according to the amount of 2MBP to be purified.

The usefulness and advantages of the present crystallization procedures is shown in the following specific Examples 1 and 2. After crystallization, the precipitated material was observed under a microscope to confirm its crystalline form. Additionally, X-ray diffraction analysis was performed. Yields of crystallizations were high and the obtained crystals showed a relatively sharp melting point of 162–164° C.

The described crystallization process of the synthetic 2MBP product represents a valuable purification method, which can remove not only some side products derived from the synthetic path, but, moreover, concomitant 1α-hydroxyvitamin $D_4$. Such impurity is the result of the contamination of natural ergosterol with its 22,23-dihydro analog.

Crystallization of 2MBP

EXAMPLE 1

Crystallization from Acetone (a) 2MBP product to be purified may be dissolved in boiling acetone (1.2 mL, Aldrich) under argon atmosphere, left at room temperature (68° F.) for a few hours (1–3 hrs) and then in a refrigerator (35–45° F.) overnight (8–12 hrs). The precipitated crystals should be filtered off, washed with a small volume of a cold (0° C.) acetone and dried.

(b) These crystals of 2MBP may then be recrystallized with acetone (0.5 mL) as described in Example 1(a). The precipitated crystals have a relatively sharp melting point of 162–164° C., and were observed under a microscope to confirm their crystalline form.

EXAMPLE 2

Experimental

A colorless plate-shaped crystal of dimensions 0.40× 0.25×0.03 mm was utilized for the structural analysis. Intensity data were collected with a Siemens HISTAR area detector mounted on a platform goniometer using Cu Kα radiation (λ=1.54178 Å) focused with Goebel optics. The crystal was mounted on a thin nylon fiber with vacuum grease and data were collected at ambient temperature, 293° K. The intensity data were measured as a series of ω oscillation frames each of 0.25°; these were comprised of 5 scans (500 images each, 40 sec./image) at detector 2θ of −85° and 2 scans (500 images each, 20 sec./image) at detector 2θ of −40°. The detector was operated in 512×512 mode and was positioned 6.0 cm from the sample. Coverage of unique data was 95.4% complete to 58.88 degrees in θ. The first 50 frames were repeated at the end of data collection and showed essentially no decay of the crystal diffraction during the data collection. A total of 6917 data was measured in the range 4.38<θ<58.88°. The data were merged and scaled to form a set of 2697 independent data with R(int)=0.0562 using SAINT (Bruker-AXS, Inc.).

The orthorhombic space group P2(1)2(1)2(1) was determined by systematic absences and statistical tests and verified by subsequent refinement. The structure was solved by direct methods and refined by full-matrix least-squares methods on $F^2$ using SHELXL-97 (G. M. Sheldrick, 1994; SHELXTL Version 5 Reference Manual, Bruker-AXS, Inc.). Hydrogen atom positions were intially located in Fourier difference maps, but refined by a riding model with idealized geometries. Non-hydrogen atoms were refined with anisotropic displacement parameters. A total of 229 parameters were refined against 0 restraints and 2697 data to give $wR(F^2)=0.1369$ and S=1.088 for weights of $w=1/[s^2 (F^2)+ (0.0824\ P)^2]$, where $P=[F_o^2+2F_c^2]/3$. The final R(F) was 0.0544 for the 2697 observed, [F>2s(F)], data. The final difference map had maxima and minima of 0.126 and −0.153 e/Å$^3$, respectively.

The three dimensional structure of 2MBP as defined by the following physical data and atomic positional parameters described and calculated herein is illustrated in FIG. 1.

TABLE I

Crystal data and structure refinement for 2-MbisP.

| | |
|---|---|
| Empirical formula | C23 H36 O2 |
| Formula weight | 344.52 |
| Temperature | 293(2) K |
| Wavelength | 1.54178 Å |
| Crystal system, space group | Orthorhombic, P2(1)2(1)2(1) |
| Unit cell dimensions | a = 6.6320(13) Å α = 90° |
| | b = 15.514(3) Å β = 90° |
| | c = 20.194(4) Å γ = 90° |
| Volume | 2077.7(7) Å$^3$ |
| Z, Calculated density | 4, 1.101 Mg/m$^3$ |
| Absorption coefficient | 0.520 mm$^{-1}$ |
| F(000) | 760 |
| Crystal size | 0.40 × 0.25 × 0.03 mm |
| Theta range for data collection | 4.38 to 58.88° |

TABLE I-continued

Crystal data and structure refinement for 2-MbisP.

| | |
|---|---|
| Limiting indices | $-7 \le h \le 5$, $-12 \le k \le 17$, $-22 \le l \le 21$ |
| Reflections collected/unique | 6917/2697 [$R_{int} = 0.0562$] |
| Completeness to theta = 25.00 | 95.4% |
| Refinement method | Full-matrix least-squares on $F^2$ |
| Data/restraints/parameters | 2697/0/229 |
| Goodness-of-fit on $F^2$ | 1.088 |
| Final R indices [I > 2 sigma(I)] | R1 = 0.0544, wR2 = 0.1369 |
| R indices (all data) | R1 = 0.0622, wR2 = 0.1453 |
| Largest diff. peak and hole | 0.126 and −0.153 e/Å$^{-3}$ |

TABLE 2

Atomic coordinates (×10$^4$) and equivalent isotropic displacement parameters (Å$^2$ × 10$^3$) for 2-MbisP. U(eq) is defined as one third of the trace of the orthogonalized Uij tensor.

| | x | y | z | U(eq) |
|---|---|---|---|---|
| O(1) | 1842(3) | 3525(1) | 5011(1) | 62(1) |
| O(3) | 7954(4) | 3113(1) | 4476(2) | 78(1) |
| C(1) | 3883(5) | 3729(2) | 4852(2) | 50(1) |
| C(2) | 4569(5) | 3359(2) | 4201(2) | 58(1) |
| C(3) | 6698(5) | 3569(2) | 4030(2) | 61(1) |
| C(4) | 7074(6) | 4537(2) | 4057(2) | 59(1) |
| C(5) | 6301(5) | 4937(2) | 4686(2) | 48(1) |
| C(6) | 7497(5) | 5433(2) | 5059(2) | 52(1) |
| C(7) | 7012(5) | 5872(2) | 5673(2) | 53(1) |
| C(8) | 8248(5) | 6371(2) | 6020(2) | 50(1) |
| C(9) | 10390(5) | 6589(2) | 5828(2) | 65(1) |
| C(10) | 4161(5) | 4704(2) | 4851(2) | 51(1) |
| C(11) | 10739(6) | 7562(2) | 5809(2) | 70(1) |
| C(12) | 10108(6) | 8006(2) | 6452(2) | 61(1) |
| C(13) | 7933(5) | 7806(2) | 6640(1) | 47(1) |
| C(14) | 7696(5) | 6814(2) | 6661(2) | 50(1) |
| C(15) | 5663(6) | 6668(2) | 6982(2) | 62(1) |
| C(16) | 5453(5) | 7416(2) | 7474(2) | 59(1) |
| C(17) | 7251(5) | 8038(2) | 7353(2) | 51(1) |
| C(18) | 6466(6) | 8205(2) | 6135(2) | 64(1) |
| C(19) | 3405(7) | 2898(3) | 3811(2) | 97(1) |
| C(20) | 6703(6) | 8967(2) | 7542(2) | 65(1) |
| C(21) | 6012(8) | 9017(3) | 8269(2) | 92(1) |
| C(22) | 8368(7) | 9636(2) | 7418(2) | 89(1) |
| C(23) | 10284(9) | 9512(3) | 7809(3) | 116(2) |

TABLE 3

Bond lengths [Å] and angles [°] for 2-MbisP.

| | | | |
|---|---|---|---|
| O(1)—C(1) | 1.426(4) | O(3)—C(3) | 1.416(4) |
| C(1)—C(2) | 1.505(5) | C(1)—C(10) | 1.524(4) |
| C(2)—C(19) | 1.314(5) | C(2)—C(3) | 1.490(5) |
| C(3)—C(4) | 1.522(4) | C(4)—C(5) | 1.504(5) |
| C(5)—C(6) | 1.335(4) | C(5)—C(10) | 1.502(5) |
| C(6)—C(7) | 1.452(4) | C(7)—C(8) | 1.327(4) |
| C(8)—C(9) | 1.511(5) | C(8)—C(14) | 1.511(4) |
| C(9)—C(11) | 1.527(5) | C(11)—C(12) | 1.530(5) |
| C(12)—C(13) | 1.523(5) | C(13)—C(18) | 1.539(5) |
| C(13)—C(14) | 1.548(4) | C(13)—C(17) | 1.553(5) |
| C(14)—C(15) | 1.513(5) | C(15)—C(16) | 1.534(5) |
| C(16)—C(17) | 1.553(5) | C(17)—C(20) | 1.535(5) |
| C(20)—C(22) | 1.536(6) | C(20)—C(21) | 1.540(5) |
| C(22)—C(23) | 1.508(7) | | |
| O(1)—C(1)—C(2) | 113.5(3) | O(1)—C(1)—C(10) | 109.6(2) |
| C(2)—C(1)—C(10) | 109.9(3) | C(19)—C(2)—C(3) | 122.5(3) |
| C(19)—C(2)—C(1) | 123.6(3) | C(3)—C(2)—C(1) | 113.9(3) |
| O(3)—C(3)—C(2) | 107.5(3) | O(3)—C(3)—C(4) | 111.9(3) |
| C(2)—C(3)—C(4) | 111.3(3) | C(5)—C(4)—C(3) | 112.5(3) |

TABLE 3-continued

Bond lengths [Å] and angles [°] for 2-MbisP.

| | | | |
|---|---|---|---|
| C(6)—C(5)—C(10) | 125.1(3) | C(6)—C(5)—C(4) | 120.7(3) |
| C(10)—C(5)—C(4) | 114.2(3) | C(5)—C(6)—C(7) | 128.3(3) |
| C(8)—C(7)—C(6) | 126.0(3) | C(7)—C(8)—C(9) | 125.1(3) |
| C(7)—C(8)—C(14) | 124.6(3) | C(9)—C(8)—C(14) | 110.3(3) |
| C(8)—C(9)—C(11) | 111.7(3) | C(5)—C(10)—C(1) | 110.8(2) |
| C(9)—C(11)—C(12) | 112.5(3) | C(13)—C(12)—C(11) | 112.2(3) |
| C(12)—C(13)—C(18) | 110.6(3) | C(12)—C(13)—C(14) | 107.8(3) |
| C(18)—C(13)—C(14) | 110.8(3) | C(12)—C(13)—C(17) | 117.3(3) |
| C(18)—C(13)—C(17) | 109.7(3) | C(14)—C(13)—C(17) | 100.1(2) |
| C(15)—C(14)—C(8) | 121.0(3) | C(15)—C(14)—C(13) | 104.6(3) |
| C(8)—C(14)—C(13) | 113.8(2) | C(14)—C(15)—C(16) | 104.2(3) |
| C(15)—C(16)—C(17) | 107.4(3) | C(20)—C(17)—C(16) | 111.3(3) |
| C(20)—C(17)—C(13) | 121.2(3) | C(16)—C(17)—C(13) | 103.0(2) |
| C(22)—C(20)—C(17) | 115.0(3) | C(22)—C(20)—C(21) | 109.6(3) |
| C(17)—C(20)—C(21) | 110.8(3) | C(23)—C(22)—C(20) | 115.7(4) |

TABLE 4

Anisotropic displacement parameters (Å$^2$ × 10$^3$) for 2-MbisP. The anisotropic displacement factor exponent takes the form:
$-2\pi^2[h^2 a^{*2} U11 + \ldots + 2 h k a^* b^* U12]$

| | U11 | U22 | U33 | U23 | U13 | U12 |
|---|---|---|---|---|---|---|
| O(1) | 36(1) | 59(1) | 92(2) | −7(1) | −3(1) | −5(1) |
| O(3) | 42(1) | 48(1) | 145(2) | 3(1) | −17(2) | 2(1) |
| C(1) | 34(2) | 45(2) | 70(2) | −5(2) | −11(2) | −1(1) |
| C(2) | 39(2) | 51(2) | 83(2) | −21(2) | −14(2) | 6(1) |
| C(3) | 55(2) | 52(2) | 75(2) | −19(2) | −7(2) | 8(2) |
| C(4) | 60(2) | 56(2) | 61(2) | −2(2) | 2(2) | 0(2) |
| C(5) | 52(2) | 34(1) | 58(2) | 3(1) | −5(2) | 1(1) |
| C(6) | 51(2) | 45(2) | 61(2) | 2(1) | 5(2) | −9(2) |
| C(7) | 56(2) | 42(2) | 62(2) | 2(1) | 6(2) | −8(2) |
| C(8) | 47(2) | 44(2) | 58(2) | 3(1) | −1(2) | −10(2) |
| C(9) | 48(2) | 75(2) | 73(2) | −15(2) | 3(2) | −12(2) |
| C(10) | 44(2) | 41(2) | 66(2) | −11(1) | −6(2) | 4(1) |
| C(11) | 59(2) | 78(2) | 72(2) | −12(2) | 11(2) | −32(2) |
| C(12) | 59(2) | 61(2) | 63(2) | −5(2) | 1(2) | −22(2) |
| C(13) | 43(2) | 51(2) | 47(2) | 5(1) | 1(2) | −7(2) |
| C(14) | 45(2) | 52(2) | 53(2) | 4(1) | −4(2) | −8(2) |
| C(15) | 53(2) | 64(2) | 69(2) | 1(2) | 9(2) | −19(2) |
| C(16) | 48(2) | 71(2) | 58(2) | 3(2) | 4(2) | 0(2) |
| C(17) | 49(2) | 53(2) | 50(2) | 1(1) | −7(2) | −1(2) |
| C(18) | 71(3) | 66(2) | 57(2) | 10(2) | −11(2) | −5(2) |
| C(19) | 53(3) | 122(4) | 117(3) | −68(3) | −9(3) | −8(2) |
| C(20) | 73(3) | 59(2) | 64(2) | −5(2) | −2(2) | 8(2) |
| C(21) | 117(4) | 82(3) | 76(2) | −16(2) | 20(3) | 9(3) |
| C(22) | 104(4) | 63(2) | 99(3) | −12(2) | 18(3) | −6(2) |
| C(23) | 107(4) | 101(4) | 140(5) | −39(3) | −4(4) | −25(3) |

TABLE 5

Hydrogen coordinates (×10$^4$) and isotropic displacement parameters (Å$^2$ × 10$^3$) for 2-MbisP.

| | x | y | z | U(eq) |
|---|---|---|---|---|
| H(1O) | 2030 | 2820 | 5188 | 75 |
| H(3O) | 9248 | 3381 | 4573 | 94 |
| H(1) | 4744 | 3489 | 5201 | 60 |
| H(3) | 6972 | 3366 | 3580 | 73 |
| H(4A) | 8510 | 4644 | 4021 | 71 |
| H(4B) | 6418 | 4808 | 3682 | 71 |
| H(6) | 8807 | 5506 | 4904 | 63 |
| H(7) | 5716 | 5796 | 5840 | 64 |
| H(9A) | 10678 | 6347 | 5395 | 78 |
| H(9B) | 11311 | 6330 | 6144 | 78 |

TABLE 5-continued

Hydrogen coordinates (×10⁴) and isotropic displacement parameters
($Å^2 × 10^3$) for 2-MbisP.

| | x | y | z | U(eq) |
|---|---|---|---|---|
| H(10A) | 3261 | 4960 | 4528 | 61 |
| H(10B) | 3817 | 4933 | 5284 | 61 |
| H(11A) | 9979 | 7806 | 5444 | 84 |
| H(11B) | 12157 | 7673 | 5728 | 84 |
| H(12A) | 10992 | 7820 | 6807 | 74 |
| H(12B) | 10264 | 8624 | 6403 | 74 |
| H(14) | 8690 | 6614 | 6986 | 60 |
| H(15A) | 5627 | 6117 | 7210 | 74 |
| H(15B) | 4592 | 6682 | 6655 | 74 |
| H(16A) | 5482 | 7201 | 7925 | 71 |
| H(16B) | 4186 | 7714 | 7405 | 71 |
| H(17) | 8337 | 7857 | 7652 | 61 |
| H(18A) | 6780 | 8804 | 6077 | 97 |
| H(18B) | 5109 | 8148 | 6295 | 97 |
| H(18C) | 6593 | 7911 | 5719 | 97 |
| H(19A) | 3904 | 2689 | 3412 | 117 |
| H(19B) | 2083 | 2780 | 3935 | 117 |
| H(20) | 5547 | 9133 | 7268 | 78 |
| H(21A) | 7037 | 8779 | 8551 | 138 |
| H(21B) | 4785 | 8697 | 8323 | 138 |
| H(21C) | 5783 | 9609 | 8388 | 138 |
| H(22A) | 8703 | 9627 | 6950 | 106 |
| H(22B) | 7832 | 10203 | 7518 | 106 |
| H(23A) | 9974 | 9502 | 8273 | 174 |
| H(23B) | 11194 | 9978 | 7717 | 174 |
| H(23C) | 10902 | 8976 | 7684 | 174 |

TABLE 6

Torsion angles [°] for 2-MbisP.

| | | | |
|---|---|---|---|
| O(1)—C(1)—C(2)—C(19) | 0.5(5) | C(10)—C(1)—C(2)—C(19) | −122.6(4) |
| O(1)—C(1)—C(2)—C(3) | 179.9(3) | C(10)—C(1)—C(2)—C(3) | 56.8(3) |
| C(19)—C(2)—C(3)—O(3) | −111.3(4) | C(1)—C(2)—C(3)—O(3) | 69.2(3) |
| C(19)—C(2)—C(3)—C(4) | 125.8(4) | C(1)—C(2)—C(3)—C(4) | −53.7(4) |
| O(3)—C(3)—C(4)—C(5) | −71.4(4) | C(2)—C(3)—C(4)—C(5) | 48.9(4) |
| C(3)—C(4)—C(5)—C(6) | 128.0(3) | C(3)—C(4)—C(5)—C(10) | −50.1(4) |
| C(10)—C(5)—C(6)—C(7) | −2.4(5) | C(4)—C(5)—C(6)—C(7) | 179.7(3) |
| C(5)—C(6)—C(7)—C(8) | −178.8(3) | C(6)—C(7)—C(8)—C(9) | 1.4(5) |
| C(6)—C(7)—C(8)—C(14) | −179.6(3) | C(7)—C(8)—C(9)—C(11) | 125.7(3) |
| C(14)—C(8)—C(9)—C(11) | −53.4(4) | C(6)—C(5)—C(10)—C(1) | −125.0(3) |
| C(4)—C(5)—C(10)—C(1) | 53.1(3) | O(1)—C(1)—C(10)—C(5) | 179.9(2) |
| C(2)—C(1)—C(10)—C(5) | −54.7(3) | C(8)—C(9)—C(11)—C(12) | 53.0(4) |
| C(9)—C(11)—C(12)—C(13) | −54.6(4) | C(11)—C(12)—C(13)—C(18) | −66.8(4) |
| C(11)—C(12)—C(13)—C(14) | 54.5(4) | C(11)—C(12)—C(13)—C(17) | 166.4(3) |
| C(7)—C(8)—C(14)—C(15) | 3.9(5) | C(9)—C(8)—C(14)—C(15) | −177.0(3) |
| C(7)—C(8)—C(14)—C(13) | −122.0(3) | C(9)—C(8)—C(14)—C(13) | 57.2(4) |
| C(12)—C(13)—C(14)—C(15) | 168.8(3) | C(18)—C(13)—C(14)—C(15) | −70.1(3) |
| C(17)—C(13)—C(14)—C(15) | 45.6(3) | C(12)—C(13)—C(14)—C(8) | −57.1(3) |
| C(18)—C(13)—C(14)—C(8) | 64.1(4) | C(17)—C(13)—C(14)—C(8) | 179.7(3) |
| C(8)—C(14)—C(15)—C(16) | −163.1(3) | C(13)—C(14)—C(15)—C(16) | −33.1(3) |
| C(14)—C(15)—C(16)—C(17) | 7.4(4) | C(15)—C(16)—C(17)—C(20) | 151.9(3) |
| C(15)—C(16)—C(17)—C(13) | 20.6(3) | C(12)—C(13)—C(17)—C(20) | 79.2(4) |
| C(18)—C(13)—C(17)—C(20) | −48.2(4) | C(14)—C(13)—C(17)—C(20) | −164.7(3) |
| C(12)—C(13)—C(17)—C(16) | −155.7(3) | C(18)—C(13)—C(17)—C(16) | 76.9(3) |
| C(14)—C(13)—C(17)—C(16) | −39.5(3) | C(16)—C(17)—C(20)—C(22) | −178.0(3) |
| C(13)—C(17)—C(20)—C(22) | −56.8(5) | C(16)—C(17)—C(20)—C(21) | 56.9(4) |
| C(13)—C(17)—C(20)—C(21) | 178.1(3) | C(17)—C(20)—C(22)—C(23) | −62.9(5) |
| C(21)—C(20)—C(22)—C(23) | 62.8(5) | | |

TABLE 7

Observed and calculated structure factors for 2-Mbis-P

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| 4 | 0 | 0 | 51 | 50 | 3 | 1 | 15 | 0 | 43 | 53 | 3 | -4 | 14 | 1 | 298 | 328 | 8 | 0 | 6 | 1 | 38 | 38 | 5 |
| 5 | 0 | 0 | 49 | 54 | 4 | 2 | 15 | 0 | 82 | 87 | 2 | -3 | 14 | 1 | 326 | 324 | 6 | 1 | 6 | 1 | 54 | 53 | 3 |
| -1 | 1 | 0 | 108 | 125 | 1 | 3 | 15 | 0 | 53 | 49 | 3 | -2 | 14 | 1 | 62 | 70 | 2 | 2 | 6 | 1 | 95 | 101 | 3 |
| 2 | 1 | 0 | 833 | 823 | 10 | 0 | 16 | 0 | 28 | 24 | 8 | -1 | 14 | 1 | 76 | 73 | 2 | 3 | 6 | 1 | 78 | 78 | 2 |
| 4 | 1 | 0 | 448 | 435 | 4 | 1 | 16 | 0 | 25 | 18 | 8 | 0 | 14 | 1 | 68 | 62 | 1 | 4 | 6 | 1 | 73 | 68 | 1 |
| 5 | 1 | 0 | 62 | 62 | 2 | 2 | 16 | 0 | 17 | 12 | 10 | 1 | 14 | 1 | 125 | 129 | 2 | 5 | 6 | 1 | 78 | 79 | 2 |
| 6 | 1 | 0 | 65 | 72 | 1 | -1 | 17 | 0 | 54 | 37 | 5 | 2 | 14 | 1 | 89 | 91 | 2 | 6 | 6 | 1 | 97 | 101 | 2 |
| 0 | 2 | 0 | 650 | 820 | 8 | 0 | 0 | 1 | 304 | 297 | 10 | 3 | 14 | 1 | 152 | 158 | 1 | -6 | 7 | 1 | 44 | 53 | 2 |
| 1 | 2 | 0 | 510 | 519 | 6 | -1 | 0 | 1 | 85 | 79 | 5 | 4 | 14 | 1 | 168 | 165 | 2 | -5 | 7 | 1 | 44 | 34 | 5 |
| 2 | 2 | 0 | 217 | 213 | 2 | 0 | 0 | 1 | 115 | 107 | 1 | -3 | 15 | 1 | 138 | 136 | 1 | -4 | 7 | 1 | 33 | 5 | 5 |
| 4 | 2 | 0 | 120 | 117 | 1 | 2 | 0 | 1 | 111 | 115 | 2 | -2 | 15 | 1 | 101 | 94 | 2 | -3 | 7 | 1 | 46 | 46 | 6 |
| 5 | 2 | 0 | 88 | 88 | 2 | 4 | 0 | 1 | 36 | 28 | 4 | 0 | 15 | 1 | 219 | 219 | 3 | -2 | 7 | 1 | 25 | 30 | 2 |
| -1 | 3 | 0 | 36 | 42 | 5 | 5 | 0 | 1 | 56 | 55 | 3 | 1 | 15 | 1 | 223 | 236 | 3 | -1 | 7 | 1 | 38 | 30 | 5 |
| 2 | 3 | 0 | 37 | 49 | 7 | -6 | 1 | 1 | 107 | 120 | 2 | 2 | 15 | 1 | 213 | 220 | 2 | 0 | 7 | 1 | 38 | 30 | 2 |
| 4 | 3 | 0 | 352 | 375 | 5 | -5 | 1 | 1 | 162 | 152 | 1 | 3 | 15 | 1 | 91 | 93 | 3 | 1 | 7 | 1 | 34 | 46 | 4 |
| 5 | 3 | 0 | 39 | 35 | 3 | -4 | 1 | 1 | 338 | 350 | 1 | -2 | 16 | 1 | 136 | 137 | 2 | 2 | 7 | 1 | 27 | 4 | 11 |
| -2 | 4 | 0 | 58 | 55 | 3 | -2 | 1 | 1 | 1141 | 1205 | 14 | -1 | 16 | 1 | 174 | 165 | 1 | 3 | 7 | 1 | 24 | 27 | 2 |
| 3 | 4 | 0 | 84 | 80 | 2 | -1 | 1 | 1 | 1134 | 1206 | 11 | 0 | 16 | 1 | 160 | 158 | 2 | 4 | 7 | 1 | 27 | 13 | 1 |
| 4 | 4 | 0 | 43 | 42 | 8 | 4 | 1 | 1 | 163 | 152 | 1 | 1 | 16 | 1 | 33 | 17 | 2 | 5 | 7 | 1 | 18 | 4 | 2 |
| 5 | 4 | 0 | 54 | 51 | 5 | 5 | 1 | 1 | 109 | 120 | 1 | 2 | 16 | 1 | 61 | 46 | 24 | 6 | 7 | 1 | 33 | 13 | 3 |
| -6 | 5 | 0 | 34 | 7 | 7 | 6 | 1 | 1 | 56 | 55 | 11 | -1 | 17 | 1 | 65 | 60 | 10 | -6 | 8 | 1 | 20 | 28 | 13 |
| -3 | 5 | 0 | 114 | 118 | 2 | -5 | 2 | 1 | 19 | 16 | 18 | 0 | 17 | 1 | 52 | 51 | 11 | -5 | 8 | 1 | 24 | 32 | 3 |
| -1 | 5 | 0 | 17 | 3 | 18 | -4 | 2 | 1 | 38 | 15 | 4 | 1 | 17 | 1 | 150 | 145 | 2 | -4 | 8 | 1 | 17 | 3 | 2 |
| 2 | 5 | 0 | 88 | 82 | 3 | -3 | 2 | 1 | 41 | 44 | 4 | -6 | 3 | 2 | 86 | 88 | 1 | -3 | 8 | 1 | 393 | 405 | 5 |
| 3 | 5 | 0 | 87 | 87 | 1 | -2 | 2 | 1 | 28 | 16 | 5 | -5 | 3 | 2 | 68 | 69 | 5 | -2 | 8 | 1 | 332 | 336 | 8 |
| 4 | 5 | 0 | 19 | 15 | 18 | -1 | 2 | 1 | 256 | 252 | 2 | -4 | 3 | 2 | 378 | 391 | 6 | -1 | 8 | 1 | 412 | 409 | 2 |
| 5 | 5 | 0 | 99 | 104 | 5 | 0 | 2 | 1 | 108 | 98 | 1 | -3 | 3 | 2 | 69 | 68 | 4 | 0 | 8 | 1 | 137 | 137 | 3 |
| -6 | 6 | 0 | 66 | 56 | 8 | 2 | 2 | 1 | 98 | 100 | 3 | -2 | 3 | 2 | 89 | 87 | 2 | 1 | 8 | 1 | 34 | 44 | 2 |
| -5 | 6 | 0 | 17 | 4 | 50 | 3 | 2 | 1 | 465 | 481 | 2 | 0 | 3 | 2 | 152 | 145 | 2 | 2 | 8 | 1 | 114 | 119 | 4 |
| -4 | 6 | 0 | 72 | 64 | 21 | 4 | 2 | 1 | 15 | 2 | 4 | 1 | 3 | 2 | 54 | 51 | 2 | 3 | 8 | 1 | 52 | 49 | 2 |
| -3 | 6 | 0 | 108 | 106 | 2 | 5 | 2 | 1 | 478 | 482 | 5 | 2 | 3 | 2 | 67 | 59 | 1 | 4 | 8 | 1 | 174 | 178 | 1 |
| -2 | 6 | 0 | 86 | 82 | 1 | -6 | 3 | 1 | 93 | 99 | 6 | 4 | 3 | 2 | 46 | 48 | 4 | 5 | 8 | 1 | 599 | 599 | 5 |
| -1 | 6 | 0 | 34 | 29 | 4 | -5 | 3 | 1 | 257 | 252 | 4 | 5 | 3 | 2 | 37 | 28 | 12 | 6 | 8 | 1 | 166 | 164 | 2 |
| 3 | 6 | 0 | 29 | 22 | 6 | -4 | 3 | 1 | 17 | 16 | 6 | -6 | 4 | 2 | 84 | 71 | 3 | -6 | 9 | 1 | 278 | 178 | 2 |
| 5 | 6 | 0 | 57 | 41 | 8 | -3 | 3 | 1 | 41 | 44 | 4 | -5 | 4 | 2 | 105 | 103 | 1 | -5 | 9 | 1 | 50 | 49 | 2 |
| -7 | 7 | 0 | 645 | 708 | 50 | -2 | 3 | 1 | 17 | 14 | 8 | -4 | 4 | 2 | 156 | 151 | 2 | -4 | 9 | 1 | 119 | 118 | 3 |
| -5 | 7 | 0 | 360 | 437 | 21 | -1 | 3 | 1 | 41 | 49 | 6 | -3 | 4 | 2 | 54 | 46 | 3 | -3 | 9 | 1 | 47 | 44 | 4 |
| 3 | 7 | 0 | 101 | 86 | 4 | 0 | 3 | 1 | 52 | 50 | 4 | -1 | 4 | 2 | 194 | 201 | 5 | -2 | 9 | 1 | 59 | 55 | 2 |
| 4 | 7 | 0 | 36 | 39 | 5 | 1 | 3 | 1 | 171 | 175 | 1 | 0 | 4 | 2 | 227 | 223 | 2 | -1 | 9 | 1 | 39 | 34 | 6 |
| 5 | 7 | 0 | 19 | 17 | 4 | 3 | 3 | 1 | 239 | 231 | 1 | 2 | 4 | 2 | 190 | 201 | 7 | 0 | 9 | 1 | 106 | 111 | 2 |
| 6 | 7 | 0 | 80 | 76 | 5 | 4 | 3 | 1 | 457 | 454 | 1 | 3 | 4 | 2 | 50 | 46 | 3 | 1 | 9 | 1 | 211 | 211 | 3 |
| -1 | 7 | 0 | 48 | 44 | 3 | 5 | 3 | 1 | 306 | 308 | 3 | 4 | 4 | 2 | 157 | 151 | 1 | 2 | 9 | 1 | 74 | 77 | 1 |
| 2 | 7 | 0 | 31 | 28 | 3 | 6 | 3 | 1 | 375 | 403 | 1 | 5 | 4 | 2 | 114 | 103 | 5 | 3 | 9 | 1 | 385 | 373 | 5 |
| 4 | 7 | 0 | 110 | 128 | 25 | -1 | 3 | 1 | 358 | 411 | 19 | 6 | 4 | 2 | 74 | 71 | 6 | 4 | 9 | 1 | 96 | 91 | 3 |
| 2 | 3 | 0 | 72 | 70 | 1 | 0 | 3 | 1 | 394 | 402 | 3 | -1 | 4 | 2 | 36 | 28 | 6 | 5 | 9 | 1 | 614 | 632 | 19 |

| h | k | l | 10Fo | 10Fc | 10s |
|---|---|---|------|------|-----|
| 1 | 5 | 2 | 153 | 145 | 7 |
| 2 | 5 | 2 | 175 | 176 | 2 |
| 3 | 5 | 2 | 156 | 167 | 5 |
| 4 | 5 | 2 | 194 | 188 | 2 |
| 5 | 5 | 2 | 99 | 96 | 2 |
| 6 | 5 | 2 | 84 | 79 | 3 |
| 7 | 5 | 2 | 70 | 47 | 4 |
| -6 | 6 | 2 | 65 | 66 | 3 |
| -5 | 6 | 2 | 60 | 66 | 2 |
| -4 | 6 | 2 | 74 | 77 | 1 |
| -3 | 6 | 2 | 130 | 128 | 3 |
| -2 | 6 | 2 | 150 | 159 | 2 |
| -1 | 6 | 2 | 233 | 248 | 3 |
| 0 | 6 | 2 | 529 | 545 | 2 |
| 1 | 6 | 2 | 238 | 248 | 3 |
| 2 | 6 | 2 | 152 | 158 | 4 |
| 3 | 6 | 2 | 131 | 128 | 2 |
| 4 | 6 | 2 | 77 | 77 | 1 |
| 5 | 6 | 2 | 61 | 66 | 2 |
| 6 | 6 | 2 | 69 | 66 | 3 |
| -6 | 7 | 2 | 39 | 49 | 13 |
| -5 | 7 | 2 | 96 | 98 | 3 |
| -4 | 7 | 2 | 65 | 63 | 2 |
| -3 | 7 | 2 | 99 | 90 | 2 |
| -2 | 7 | 2 | 141 | 157 | 5 |
| -1 | 7 | 2 | 442 | 439 | 5 |
| 0 | 7 | 2 | 252 | 268 | 2 |
| 1 | 7 | 2 | 447 | 419 | 14 |
| 2 | 7 | 2 | 146 | 157 | 2 |
| 3 | 7 | 2 | 99 | 89 | 1 |
| 4 | 7 | 2 | 69 | 63 | 2 |
| 5 | 7 | 2 | 102 | 97 | 2 |
| 6 | 7 | 2 | 51 | 48 | 4 |
| -6 | 8 | 2 | 20 | 16 | 13 |
| -5 | 8 | 2 | 53 | 52 | 4 |
| -4 | 8 | 2 | 118 | 118 | 2 |
| -3 | 8 | 2 | 92 | 90 | 2 |
| -2 | 8 | 2 | 40 | 37 | 2 |
| -1 | 8 | 2 | 325 | 343 | 4 |
| 0 | 8 | 2 | 165 | 266 | 4 |
| 1 | 8 | 2 | 312 | 455 | 2 |
| 2 | 8 | 2 | 38 | 37 | 1 |
| 3 | 8 | 2 | 92 | 91 | 3 |
| 4 | 8 | 2 | 118 | 118 | 3 |
| 5 | 8 | 2 | 54 | 52 | 4 |

TABLE 7-continued

Observed and calculated structure factors for 2-Mbis-P

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| 4 | 7 | 0 | 79 | 78 | 2 | 2 | 3 | 1 | 304 | 307 | 4 | -5 | 10 | 1 | 54 | 57 | 4 | 0 | 2 | 2 | 371 | 373 | 7 | 6 | 8 | 2 | 32 | 16 | 15 |
| 5 | 7 | 0 | 171 | 167 | 2 | 3 | 3 | 1 | 472 | 455 | 6 | -4 | 10 | 1 | 107 | 110 | 6 | 1 | 2 | 2 | 623 | 632 | 8 | -6 | 9 | 2 | 76 | 71 | 5 |
| 6 | 7 | 0 | 49 | 48 | 4 | 4 | 3 | 1 | 240 | 231 | 2 | -3 | 10 | 1 | 168 | 166 | 2 | 2 | 2 | 2 | 105 | 92 | 2 | -5 | 9 | 2 | 42 | 36 | 6 |
| 0 | 8 | 0 | 134 | 137 | 2 | 5 | 3 | 1 | 169 | 176 | 3 | -2 | 10 | 1 | 79 | 78 | 3 | 3 | 2 | 2 | 80 | 78 | 1 | -4 | 9 | 2 | 170 | 164 | 2 |
| 1 | 8 | 0 | 226 | 226 | 8 | 6 | 3 | 1 | 44 | 50 | 5 | -1 | 10 | 1 | 139 | 149 | 2 | 4 | 2 | 2 | 211 | 211 | 6 | -3 | 9 | 2 | 83 | 82 | 1 |
| 2 | 8 | 0 | 211 | 196 | 3 | 7 | 3 | 1 | 54 | 49 | 5 | 0 | 10 | 1 | 127 | 138 | 1 | 5 | 2 | 2 | 116 | 111 | 3 | -2 | 9 | 2 | 44 | 39 | 2 |
| 3 | 8 | 0 | 66 | 64 | 3 | -7 | 4 | 1 | 46 | 41 | 5 | 1 | 10 | 1 | 145 | 148 | 1 | 6 | 2 | 2 | 34 | 35 | 7 | -1 | 9 | 2 | 77 | 79 | 1 |
| 4 | 8 | 0 | 315 | 302 | 2 | -6 | 4 | 1 | 81 | 84 | 2 | 2 | 10 | 1 | 74 | 79 | 1 | 0 | 3 | 2 | 69 | 71 | 4 | 0 | 9 | 2 | 64 | 93 | 3 |
| 5 | 8 | 0 | 67 | 53 | 5 | -5 | 4 | 1 | 36 | 26 | 6 | 3 | 10 | 1 | 168 | 165 | 1 | 1 | 3 | 2 | 75 | 81 | 4 | 1 | 9 | 2 | 80 | 79 | 2 |
| 6 | 8 | 0 | 38 | 28 | 6 | -4 | 4 | 1 | 171 | 165 | 1 | 4 | 10 | 1 | 107 | 110 | 1 | 2 | 3 | 2 | 112 | 104 | 1 | 2 | 9 | 2 | 40 | 38 | 5 |
| 0 | 9 | 0 | 247 | 260 | 2 | -3 | 4 | 1 | 189 | 193 | 1 | 5 | 10 | 1 | 62 | 57 | 4 | 3 | 3 | 2 | 147 | 144 | 2 | 3 | 9 | 2 | 85 | 82 | 1 |
| 1 | 9 | 0 | 243 | 244 | 2 | -2 | 4 | 1 | 199 | 199 | 3 | -5 | 11 | 1 | 22 | 6 | 13 | 4 | 3 | 2 | 190 | 177 | 2 | 4 | 9 | 2 | 172 | 164 | 2 |
| 2 | 9 | 0 | 193 | 186 | 3 | -1 | 4 | 1 | 346 | 367 | 3 | -4 | 11 | 1 | 77 | 79 | 2 | 5 | 3 | 2 | 105 | 107 | 2 | 5 | 9 | 2 | 25 | 36 | 9 |
| 3 | 9 | 0 | 405 | 398 | 3 | 0 | 4 | 1 | 450 | 520 | 1 | -3 | 11 | 1 | 31 | 50 | 1 | -6 | 4 | 2 | 395 | 396 | 14 | 6 | 9 | 2 | 77 | 77 | 8 |
| 4 | 9 | 0 | 8 | 2 | 8 | 1 | 4 | 1 | 356 | 368 | 1 | -2 | 11 | 1 | 70 | 71 | 1 | -5 | 4 | 2 | 252 | 272 | 12 | -5 | 10 | 2 | 29 | 11 | 11 |
| 5 | 9 | 0 | 91 | 75 | 7 | 2 | 4 | 1 | 195 | 200 | 2 | -1 | 11 | 1 | 92 | 93 | 2 | -4 | 4 | 2 | 391 | 396 | 5 | -4 | 10 | 2 | 100 | 99 | 4 |
| 6 | 9 | 0 | 119 | 124 | 3 | 3 | 4 | 1 | 182 | 194 | 3 | 0 | 11 | 1 | 98 | 100 | 3 | -3 | 4 | 2 | 108 | 107 | 2 | -3 | 10 | 2 | 176 | 168 | 3 |
| 0 | 10 | 0 | 54 | 49 | 2 | 4 | 4 | 1 | 176 | 166 | 1 | 1 | 11 | 1 | 94 | 93 | 1 | -2 | 4 | 2 | 146 | 144 | 1 | -2 | 10 | 2 | 145 | 135 | 3 |
| 1 | 10 | 0 | 127 | 124 | 1 | 5 | 4 | 1 | 37 | 26 | 4 | 2 | 11 | 1 | 58 | 71 | 1 | -1 | 4 | 2 | 108 | 103 | 2 | -1 | 10 | 2 | 167 | 159 | 3 |
| 2 | 10 | 0 | 116 | 115 | 2 | 6 | 4 | 1 | 83 | 84 | 3 | 3 | 11 | 1 | 52 | 50 | 2 | 0 | 4 | 2 | 89 | 81 | 2 | 0 | 10 | 2 | 187 | 189 | 3 |
| 3 | 10 | 0 | 26 | 0 | 5 | -7 | 5 | 1 | 37 | 41 | 6 | 4 | 11 | 1 | 79 | 79 | 4 | 1 | 4 | 2 | 75 | 70 | 3 | 1 | 10 | 2 | 168 | 158 | 2 |
| 4 | 10 | 0 | 63 | 63 | 4 | -6 | 5 | 1 | 58 | 45 | 4 | -5 | 11 | 1 | 49 | 46 | 5 | 2 | 4 | 2 | 95 | 101 | 1 | 2 | 10 | 2 | 142 | 135 | 2 |
| 5 | 10 | 0 | 77 | 75 | 2 | -5 | 5 | 1 | 26 | 18 | 16 | -4 | 11 | 1 | 40 | 35 | 6 | 3 | 4 | 2 | 75 | 79 | 3 | 3 | 10 | 2 | 177 | 168 | 1 |
| 0 | 11 | 0 | 46 | 45 | 5 | -4 | 5 | 1 | 79 | 76 | 2 | -3 | 11 | 1 | 52 | 55 | 2 | 4 | 4 | 2 | 172 | 175 | 2 | 4 | 10 | 2 | 99 | 100 | 3 |
| 1 | 11 | 0 | 15 | 15 | 5 | -3 | 5 | 1 | 44 | 46 | 4 | -2 | 11 | 1 | 162 | 161 | 1 | 5 | 4 | 2 | 241 | 230 | 5 | 5 | 10 | 2 | 33 | 11 | 14 |
| 2 | 11 | 0 | 142 | 141 | 2 | -2 | 5 | 1 | 136 | 137 | 2 | -1 | 11 | 1 | 159 | 150 | 2 | -4 | 5 | 2 | 431 | 439 | 1 | -5 | 11 | 2 | 69 | 66 | 3 |
| 3 | 11 | 0 | 46 | 35 | 4 | -1 | 5 | 1 | 337 | 336 | 2 | 0 | 11 | 1 | 111 | 117 | 1 | -3 | 5 | 2 | 58 | 62 | 2 | -4 | 11 | 2 | 49 | 45 | 2 |
| 4 | 11 | 0 | 58 | 55 | 4 | 0 | 5 | 1 | 171 | 174 | 2 | 1 | 11 | 1 | 163 | 151 | 1 | -2 | 5 | 2 | 242 | 268 | 2 | -3 | 11 | 2 | 87 | 87 | 2 |
| 5 | 11 | 0 | 67 | 69 | 3 | 1 | 5 | 1 | 274 | 294 | 1 | 2 | 11 | 1 | 158 | 161 | 1 | -1 | 5 | 2 | 69 | 63 | 5 | -2 | 11 | 2 | 103 | 103 | 4 |
| 0 | 12 | 0 | 145 | 145 | 5 | 2 | 5 | 1 | 174 | 174 | 1 | 3 | 11 | 1 | 56 | 55 | 5 | 0 | 5 | 2 | 438 | 438 | 2 | -1 | 11 | 2 | 49 | 45 | 4 |
| 1 | 12 | 0 | 43 | 40 | 2 | 3 | 5 | 1 | 343 | 336 | 4 | 4 | 11 | 1 | 32 | 35 | 4 | 1 | 5 | 2 | 247 | 229 | 2 | 0 | 11 | 2 | 87 | 87 | 2 |
| 2 | 12 | 0 | 43 | 40 | 2 | 4 | 5 | 1 | 126 | 137 | 2 | -4 | 12 | 1 | 48 | 46 | 4 | 2 | 5 | 2 | 177 | 175 | 2 | 1 | 11 | 2 | 106 | 88 | 3 |
| 3 | 12 | 0 | 32 | 24 | 4 | 5 | 5 | 1 | 45 | 45 | 5 | -3 | 12 | 1 | 41 | 47 | 3 | 3 | 5 | 2 | 80 | 79 | 3 | 2 | 11 | 2 | 96 | 66 | 2 |
| 4 | 12 | 0 | 45 | 36 | 4 | 6 | 5 | 1 | 92 | 76 | 2 | -2 | 12 | 1 | 45 | 38 | 3 | 4 | 5 | 2 | 101 | 40 | 5 | 3 | 11 | 2 | 59 | 63 | 2 |
| 5 | 12 | 0 | 26 | 9 | 7 | -6 | 6 | 1 | 24 | 18 | 13 | -1 | 12 | 1 | 23 | 25 | 3 | -4 | 6 | 2 | 50 | 40 | 5 | 4 | 11 | 2 | 65 | 59 | 3 |
| 0 | 13 | 0 | 161 | 164 | 2 | -5 | 6 | 1 | 88 | 91 | 3 | 0 | 12 | 1 | 54 | 38 | 3 | -3 | 6 | 2 | 85 | 79 | 3 | -4 | 12 | 2 | 46 | 48 | 6 |
| 1 | 13 | 0 | 137 | 141 | 3 | -4 | 6 | 1 | 87 | 91 | 2 | 1 | 12 | 1 | 50 | 47 | 5 | -2 | 6 | 2 | 94 | 96 | 3 | -3 | 12 | 2 | 39 | 46 | 9 |
| 2 | 13 | 0 | 43 | 42 | 4 | -3 | 6 | 1 | 125 | 128 | 3 | 2 | 12 | 1 | 70 | 71 | 3 | -1 | 6 | 2 | 188 | 188 | 4 | -2 | 12 | 2 | 43 | 27 | 6 |
| 3 | 13 | 0 | 79 | 84 | 2 | -2 | 6 | 1 | 61 | 61 | 2 | 3 | 12 | 1 | 41 | 23 | 7 | 0 | 6 | 2 | 162 | 167 | 4 | -1 | 12 | 2 | 21 | 13 | 20 |
| 4 | 13 | 0 | 40 | 32 | 2 | -1 | 6 | 1 | 77 | 73 | 2 | -4 | 13 | 1 | 72 | 67 | 4 | 1 | 6 | 2 | 181 | 176 | 3 | 0 | 12 | 2 | 70 | 68 | 3 |
| 0 | 14 | 0 | 32 | 26 | 4 | 0 | 6 | 1 | 73 | 71 | 3 | -3 | 13 | 1 | 65 | 63 | 2 | 2 | 6 | 2 | 151 | 146 | 5 | 1 | 12 | 2 | 81 | 80 | 6 |
| 1 | 14 | 0 | 87 | 89 | 1 | 1 | 6 | 1 | 327 | 325 | 3 | -2 | 13 | 1 | 141 | 137 | 3 | 3 | 6 | 2 | 901 | 990 | 15 | 2 | 12 | 2 | 49 | 49 | 9 |
| 2 | 14 | 0 | 49 | 43 | 4 | 2 | 6 | 1 | 305 | 297 | 2 | -1 | 13 | 1 | 159 | 153 | 3 | -4 | 7 | 2 | 316 | 326 | 8 | -3 | 12 | 2 | 81 | 79 | 3 |
| 1 | 12 | 2 | 38 | 27 | 3 | 3 | 6 | 1 | 115 | 120 | 3 | 2 | 12 | 2 | 72 | 67 | 3 | -3 | 7 | 2 | 11 | 8 | 10 | | | | | | |
| 2 | 13 | 2 | 41 | 46 | 2 | 4 | 6 | 1 | 65 | 63 | 3 | 2 | 12 | 2 | 65 | 63 | 2 | -2 | 7 | 2 | 38 | 44 | 3 | | | | | | |
| 3 | 12 | 2 | 43 | 48 | 2 | -4 | 7 | 1 | 86 | 85 | 3 | 2 | 11 | 3 | 141 | 137 | 3 | -1 | 7 | 2 | 49 | 49 | 1 | | | | | | |
| 4 | 12 | 2 | 66 | 59 | 3 | -3 | 7 | 1 | 139 | 136 | 3 | 3 | 11 | 3 | 159 | 153 | 3 | 0 | 7 | 2 | 81 | 79 | 3 | | | | | | |

TABLE 7-continued

Observed and calculated structure factors for 2-Mbis-P

| h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|
| 5 | 12 | 2 | 33 | 63 | 9 | 6 | 4 | 3 | 72 | 68 | 4 | 2 | 3 | 4 | 70 | 67 | 2 |
| 4 | 13 | 2 | 34 | 34 | 8 | 7 | 4 | 3 | 48 | 42 | 5 | 3 | 10 | 4 | 105 | 104 | 2 |
| 3 | 13 | 2 | 87 | 90 | 2 | -6 | 5 | 3 | 52 | 51 | 11 | 4 | 10 | 4 | 77 | 68 | 2 |
| 2 | 13 | 2 | 36 | 20 | 5 | -5 | 5 | 3 | 172 | 171 | 2 | 5 | 10 | 4 | 58 | 60 | 3 |
| 1 | 13 | 2 | 116 | 120 | 2 | -4 | 5 | 3 | 76 | 72 | 7 | -5 | 11 | 4 | 119 | 116 | 2 |
| 0 | 13 | 2 | 66 | 62 | 2 | -3 | 5 | 3 | 21 | 12 | 20 | -4 | 11 | 4 | 24 | 11 | 7 |
| -1 | 13 | 2 | 117 | 120 | 2 | -2 | 5 | 3 | 223 | 216 | 2 | -3 | 11 | 4 | 113 | 111 | 2 |
| -2 | 13 | 2 | 30 | 20 | 7 | -1 | 5 | 3 | 186 | 196 | 2 | -2 | 11 | 4 | 86 | 83 | 2 |
| -3 | 13 | 2 | 89 | 90 | 2 | 0 | 5 | 3 | 733 | 738 | 2 | -1 | 11 | 4 | 154 | 160 | 2 |
| -4 | 13 | 2 | 38 | 34 | 4 | 1 | 5 | 3 | 197 | 196 | 2 | 0 | 11 | 4 | 109 | 111 | 2 |
| 4 | 13 | 2 | 60 | 57 | 5 | 2 | 5 | 3 | 225 | 217 | 2 | 1 | 11 | 4 | 152 | 151 | 2 |
| 3 | 14 | 2 | 41 | 43 | 8 | 3 | 5 | 3 | 15 | 12 | 46 | 2 | 11 | 4 | 83 | 83 | 2 |
| 2 | 14 | 2 | 56 | 61 | 2 | 4 | 5 | 3 | 79 | 73 | 3 | 3 | 11 | 4 | 117 | 111 | 2 |
| 1 | 14 | 2 | 34 | 25 | 5 | -4 | 5 | 3 | 176 | 171 | 2 | 4 | 11 | 4 | 32 | 12 | 6 |
| 0 | 14 | 2 | 92 | 92 | 2 | -3 | 5 | 3 | 54 | 51 | 4 | -5 | 12 | 4 | 112 | 115 | 2 |
| -1 | 14 | 2 | 22 | 25 | 7 | 5 | 5 | 3 | 52 | 51 | 5 | -4 | 12 | 4 | 59 | 47 | 8 |
| -2 | 14 | 2 | 61 | 61 | 2 | 6 | 6 | 3 | 93 | 93 | 3 | -3 | 12 | 4 | 19 | 4 | 10 |
| -3 | 14 | 2 | 41 | 42 | 4 | -6 | 6 | 3 | 120 | 114 | 2 | -2 | 12 | 4 | 116 | 121 | 2 |
| -4 | 14 | 2 | 53 | 57 | 4 | -5 | 6 | 3 | 62 | 60 | 2 | -1 | 12 | 4 | 44 | 32 | 5 |
| 3 | 14 | 2 | 36 | 36 | 7 | -4 | 6 | 3 | 238 | 243 | 2 | 0 | 12 | 4 | 125 | 117 | 2 |
| 2 | 15 | 2 | 47 | 44 | 4 | -3 | 6 | 3 | 88 | 86 | 2 | 1 | 12 | 4 | 54 | 62 | 3 |
| 1 | 15 | 2 | 21 | 10 | 7 | -2 | 6 | 3 | 136 | 146 | 2 | 2 | 12 | 4 | 119 | 117 | 2 |
| 0 | 15 | 2 | 33 | 36 | 5 | -1 | 6 | 3 | 92 | 84 | 2 | 3 | 12 | 4 | 41 | 32 | 3 |
| -1 | 15 | 2 | 25 | 10 | 8 | 0 | 6 | 3 | 233 | 242 | 2 | 4 | 12 | 4 | 120 | 121 | 2 |
| -2 | 15 | 2 | 40 | 44 | 4 | 1 | 6 | 3 | 61 | 61 | 4 | -4 | 13 | 4 | 31 | 4 | 31 |
| -3 | 15 | 2 | 34 | 37 | 4 | 2 | 6 | 3 | 125 | 114 | 2 | -3 | 13 | 4 | 46 | 47 | 5 |
| 2 | 15 | 2 | 24 | 16 | 5 | 3 | 6 | 3 | 97 | 93 | 2 | -2 | 13 | 4 | 59 | 56 | 3 |
| 1 | 16 | 2 | 27 | 29 | 7 | 4 | 6 | 3 | 58 | 51 | 3 | -1 | 13 | 4 | 77 | 80 | 2 |
| 0 | 16 | 2 | 37 | 29 | 4 | 5 | 6 | 3 | 32 | 23 | 5 | 0 | 13 | 4 | 98 | 98 | 2 |
| -1 | 16 | 2 | 29 | 16 | 7 | -6 | 6 | 3 | 33 | 57 | 6 | 1 | 13 | 4 | 37 | 42 | 2 |
| -2 | 16 | 2 | 23 | 14 | 8 | -5 | 7 | 3 | 232 | 230 | 2 | 2 | 13 | 4 | 58 | 64 | 2 |
| 1 | 16 | 2 | 19 | 28 | 11 | -4 | 7 | 3 | 59 | 56 | 2 | 3 | 13 | 4 | 40 | 42 | 2 |
| 0 | 17 | 3 | 37 | 28 | 5 | -3 | 7 | 3 | 171 | 151 | 2 | 4 | 13 | 4 | 98 | 99 | 2 |
| -1 | 17 | 3 | 986 | 1006 | 2 | -2 | 7 | 3 | 228 | 222 | 2 | -4 | 14 | 4 | 76 | 80 | 2 |
| 2 | 0 | 3 | 115 | 121 | 5 | -1 | 7 | 3 | 379 | 403 | 2 | -3 | 14 | 4 | 50 | 57 | 2 |
| 4 | 0 | 3 | 324 | 311 | 2 | 0 | 7 | 3 | 230 | 222 | 2 | -2 | 14 | 4 | 62 | 58 | 2 |
| 6 | 0 | 3 | 56 | 51 | 14 | 1 | 7 | 3 | 167 | 180 | 2 | -1 | 14 | 4 | 67 | 64 | 2 |
| 6 | 1 | 3 | 73 | 67 | 2 | 2 | 7 | 3 | 57 | 56 | 7 | 0 | 14 | 4 | 22 | 14 | 5 |
| 5 | 1 | 3 | 253 | 250 | 2 | 3 | 7 | 3 | 231 | 230 | 2 | 1 | 14 | 4 | 38 | 39 | 2 |
| 4 | 1 | 3 | 176 | 170 | 2 | 4 | 7 | 3 | 59 | 57 | 3 | 2 | 14 | 4 | 77 | 83 | 2 |
| 3 | 1 | 3 | 392 | 392 | 2 | -3 | 7 | 3 | 38 | 23 | 7 | 3 | 14 | 4 | 38 | 39 | 4 |
| 2 | 1 | 3 | 207 | 207 | 2 | 5 | 7 | 3 | 32 | 28 | 16 | 4 | 14 | 4 | 20 | 15 | 9 |
| 1 | 1 | 3 | 101 | 95 | 2 | -6 | 8 | 3 | 31 | 15 | 10 | -3 | 15 | 4 | 64 | 64 | 4 |
| 0 | 1 | 3 | 1115 | 1114 | 2 | -5 | 8 | 3 | 42 | 36 | 4 | -2 | 15 | 4 | 56 | 59 | 2 |
| -1 | 1 | 3 | 97 | 96 | 3 | -4 | 8 | 3 | 68 | 76 | 2 | -1 | 15 | 4 | 42 | 42 | 2 |
| -2 | 1 | 3 | 205 | 206 | 2 | -3 | 8 | 3 | 78 | 78 | 2 | -2 | 15 | 4 | 56 | 66 | 5 |

TABLE 7-continued

Observed and calculated structure factors for 2-Mbis-P

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| 4 | 1 | 3 | 176 | 169 | 2 | -1 | 8 | 3 | 310 | 324 | 4 | -1 | 7 | 4 | 302 | 287 | 4 | -1 | 15 | 4 | 49 | 55 | 8 |
| 5 | 1 | 3 | 252 | 249 | 5 | 0 | 8 | 3 | 234 | 243 | 11 | 0 | 7 | 4 | 175 | 175 | 14 | 0 | 15 | 4 | 44 | 36 | 3 |
| 6 | 1 | 3 | 69 | 66 | 2 | 1 | 8 | 3 | 308 | 325 | 7 | 1 | 7 | 4 | 299 | 287 | 4 | 1 | 15 | 4 | 61 | 55 | 3 |
| 7 | 1 | 3 | 42 | 18 | 6 | 2 | 8 | 3 | 185 | 191 | 3 | 2 | 7 | 4 | 142 | 175 | 2 | 2 | 15 | 4 | 54 | 66 | 4 |
| 4 | 2 | 3 | 77 | 80 | 2 | 3 | 8 | 3 | 188 | 191 | 2 | 3 | 7 | 4 | 39 | 287 | 2 | 3 | 15 | 4 | 46 | 42 | 7 |
| 5 | 2 | 3 | 59 | 70 | 2 | 4 | 8 | 3 | 79 | 78 | 2 | 4 | 7 | 4 | 58 | 139 | 2 | -2 | 16 | 4 | 36 | 41 | 8 |
| 6 | 2 | 3 | 87 | 91 | 3 | 5 | 8 | 3 | 27 | 15 | 4 | 5 | 7 | 4 | 108 | 36 | 5 | -1 | 16 | 4 | 55 | 66 | 2 |
| 5 | 3 | 3 | 223 | 231 | 3 | 6 | 8 | 3 | 25 | 28 | 2 | -6 | 8 | 4 | 69 | 57 | 7 | 0 | 16 | 4 | 24 | 6 | 6 |
| 4 | 3 | 3 | 377 | 364 | 3 | 5 | 9 | 3 | 59 | 52 | 3 | -5 | 8 | 4 | 45 | 106 | 2 | 1 | 16 | 4 | 61 | 65 | 4 |
| 3 | 3 | 3 | 725 | 744 | 16 | 4 | 9 | 3 | 82 | 80 | 3 | -4 | 8 | 4 | 176 | 36 | 5 | 2 | 16 | 4 | 32 | 41 | 7 |
| 2 | 3 | 3 | 1539 | 1543 | 19 | 3 | 9 | 3 | 261 | 247 | 4 | -3 | 8 | 4 | 86 | 36 | 2 | 0 | 0 | 5 | 97 | 112 | 2 |
| 1 | 3 | 3 | 723 | 744 | 8 | 2 | 9 | 3 | 116 | 117 | 2 | -2 | 8 | 4 | 207 | 177 | 6 | 1 | 0 | 5 | 323 | 371 | 45 |
| 0 | 3 | 3 | 359 | 364 | 4 | 1 | 9 | 3 | 72 | 67 | 3 | -1 | 8 | 4 | 119 | 93 | 3 | 2 | 0 | 5 | 180 | 174 | 2 |
| -1 | 3 | 3 | 83 | 91 | 1 | 0 | 9 | 3 | 40 | 31 | 3 | 0 | 8 | 4 | 231 | 208 | 6 | 3 | 0 | 5 | 115 | 109 | 2 |
| -2 | 3 | 3 | 63 | 70 | 1 | -1 | 9 | 3 | 52 | 55 | 2 | 1 | 8 | 4 | 180 | 121 | 6 | 4 | 0 | 5 | 316 | 289 | 4 |
| -3 | 3 | 3 | 86 | 80 | 3 | -2 | 9 | 3 | 32 | 31 | 1 | 2 | 8 | 4 | 236 | 230 | 10 | 5 | 0 | 5 | 62 | 62 | 4 |
| -4 | 3 | 3 | 25 | 20 | 11 | -3 | 9 | 3 | 69 | 67 | 1 | 3 | 8 | 4 | 124 | 122 | 7 | -6 | 1 | 5 | 209 | 197 | 3 |
| -5 | 3 | 3 | 79 | 84 | 4 | -4 | 9 | 3 | 30 | 20 | 1 | 4 | 8 | 4 | 211 | 208 | 2 | -5 | 1 | 5 | 138 | 128 | 2 |
| -6 | 3 | 3 | 127 | 121 | 2 | -5 | 9 | 3 | 203 | 150 | 4 | 5 | 8 | 4 | 91 | 93 | 2 | -4 | 1 | 5 | 101 | 112 | 2 |
| 5 | 4 | 3 | 217 | 214 | 8 | -6 | 9 | 3 | 136 | 129 | 5 | -5 | 9 | 4 | 181 | 177 | 2 | -3 | 1 | 5 | 261 | 256 | 2 |
| 4 | 4 | 3 | 87 | 77 | 2 | 6 | 10 | 3 | 329 | 324 | 9 | -4 | 9 | 4 | 46 | 36 | 6 | -2 | 1 | 5 | 290 | 294 | 6 |
| 3 | 4 | 3 | 217 | 219 | 2 | 5 | 10 | 3 | 236 | 241 | 2 | -3 | 9 | 4 | 48 | 41 | 3 | -1 | 1 | 5 | 244 | 248 | 2 |
| 2 | 4 | 3 | 676 | 688 | 22 | 4 | 10 | 3 | 471 | 497 | 15 | -2 | 9 | 4 | 51 | 48 | 2 | 0 | 1 | 5 | 287 | 295 | 3 |
| 1 | 4 | 3 | 461 | 472 | 10 | 3 | 10 | 3 | 952 | 922 | 20 | -1 | 9 | 4 | 107 | 104 | 3 | 1 | 1 | 5 | 249 | 257 | 2 |
| 0 | 4 | 3 | 675 | 687 | 5 | 2 | 10 | 3 | 483 | 497 | 8 | 0 | 9 | 4 | 74 | 74 | 1 | 2 | 1 | 5 | 135 | 128 | 3 |
| -1 | 4 | 3 | 228 | 219 | 3 | 1 | 10 | 3 | 232 | 242 | 3 | 1 | 9 | 4 | 101 | 98 | 2 | 3 | 1 | 5 | 201 | 197 | 3 |
| -2 | 4 | 3 | 220 | 213 | 2 | 0 | 10 | 3 | 125 | 129 | 3 | 2 | 9 | 4 | 72 | 69 | 3 | 4 | 1 | 5 | 76 | 61 | 1 |
| -3 | 4 | 3 | 130 | 120 | 7 | -1 | 10 | 3 | 203 | 191 | 1 | 3 | 9 | 4 | 176 | 174 | 3 | 5 | 1 | 5 | 25 | 46 | 10 |
| -4 | 4 | 3 | 81 | 84 | 3 | -2 | 10 | 3 | 27 | 20 | 11 | 4 | 9 | 4 | 66 | 69 | 4 | -6 | 2 | 5 | 118 | 119 | 2 |
| -5 | 4 | 3 | 54 | 45 | 5 | -3 | 10 | 3 | 38 | 9 | 7 | 5 | 9 | 4 | 102 | 97 | 1 | -5 | 2 | 5 | 32 | 44 | 4 |
| -6 | 4 | 3 | 69 | 68 | 2 | -4 | 10 | 3 | 82 | 78 | 3 | -4 | 10 | 4 | 78 | 73 | 4 | -4 | 2 | 5 | 224 | 218 | 4 |
| 6 | 5 | 3 | 135 | 136 | 3 | -5 | 10 | 3 | 44 | 44 | 7 | -3 | 10 | 4 | 104 | 104 | 2 | -3 | 2 | 5 | 262 | 273 | 2 |
| 5 | 5 | 3 | 79 | 85 | 2 | 5 | 11 | 3 | 15 | 9 | 7 | -2 | 10 | 4 | 53 | 48 | 5 | -2 | 2 | 5 | 713 | 749 | 40 |
| 4 | 5 | 3 | 109 | 103 | 9 | 4 | 11 | 3 | 275 | 287 | 4 | -1 | 10 | 4 | 36 | 41 | 4 | -1 | 2 | 5 | 403 | 403 | 3 |
| 3 | 5 | 3 | 119 | 121 | 3 | 3 | 11 | 3 | 262 | 259 | 8 | 0 | 10 | 4 | 59 | 60 | 8 | 0 | 2 | 5 | 716 | 750 | 7 |
| 2 | 5 | 3 | 300 | 297 | 2 | 2 | 11 | 3 | 315 | 325 | 2 | 1 | 10 | 4 | 74 | 66 | 3 | 1 | 2 | 5 | 262 | 272 | 3 |
| 1 | 5 | 3 | 261 | 268 | 4 | 1 | 11 | 3 | 241 | 241 | 3 | 2 | 10 | 4 | 104 | 104 | 2 | 2 | 2 | 5 | 41 | 44 | 1 |
| 0 | 5 | 3 | 124 | 119 | 5 | 0 | 11 | 3 | 35 | 28 | 3 | 3 | 10 | 4 | 59 | 52 | 2 | 3 | 2 | 5 | 71 | 165 | 3 |
| -1 | 5 | 3 | 66 | 56 | 4 | -1 | 11 | 3 | 147 | 143 | 3 | 4 | 10 | 4 | 92 | 97 | 7 | 4 | 2 | 5 | 151 | 142 | 3 |
| -2 | 5 | 3 | 38 | 37 | 5 | -2 | 11 | 3 | 127 | 134 | 3 | 5 | 10 | 4 | 34 | 22 | 6 | 5 | 2 | 5 | 314 | 293 | 3 |
| -3 | 5 | 3 | 78 | 76 | 3 | -3 | 11 | 3 | 361 | 357 | 3 | -4 | 11 | 4 | 129 | 126 | 1 | -6 | 4 | 5 | 148 | 130 | 1 |
| -4 | 5 | 3 | 105 | 98 | 2 | 3 | 11 | 3 | 287 | 275 | 2 | -3 | 11 | 4 | 30 | 29 | 5 | -5 | 4 | 5 | 302 | 292 | 3 |
| -5 | 5 | 3 | 226 | 216 | 2 | 2 | 11 | 3 | 283 | 262 | 5 | -2 | 11 | 4 | 113 | 115 | 2 | -4 | 4 | 5 | 174 | 165 | 4 |
| 6 | 6 | 3 | 206 | 194 | 2 | 1 | 11 | 3 | 273 | 276 | 2 | -1 | 11 | 4 | 170 | 176 | 2 | -3 | 4 | 5 | 75 | 79 | 3 |
| 5 | 6 | 3 | 158 | 136 | 4 | 0 | 11 | 3 | 356 | 357 | 4 | 0 | 11 | 4 | 23 | 20 | 2 | -2 | 4 | 5 | 80 | 78 | 3 |
| 4 | 6 | 3 | 353 | 335 | 5 | -1 | 11 | 3 | 145 | 143 | 3 | 1 | 11 | 4 | 170 | 176 | 2 | -1 | 4 | 5 | 82 | 81 | 4 |

TABLE 7-continued

Observed and calculated structure factors for 2-Mbis-P

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| 4 | 3 | 5 | 159 | 136 | 3 | -5 | 11 | 5 | 33 | 27 | 6 | 5 | 3 | 6 | 201 | 198 | 3 | 2 | 11 | 6 | 111 | 116 | 2 | -4 | 5 | 7 | 61 | 60 | 3 |
| 4 | 3 | 5 | 99 | 97 | 3 | -4 | 11 | 5 | 90 | 84 | 2 | 6 | 3 | 6 | 61 | 50 | 5 | 3 | 11 | 6 | 31 | 29 | 16 | -3 | 5 | 7 | 107 | 104 | 1 |
| 5 | 3 | 5 | 80 | 76 | 3 | -3 | 11 | 5 | 29 | 27 | 3 | -3 | 4 | 6 | 86 | 87 | 2 | 4 | 11 | 6 | 124 | 125 | 3 | -2 | 5 | 7 | 162 | 153 | 4 |
| 6 | 3 | 5 | 60 | 51 | 5 | -2 | 11 | 5 | 104 | 99 | 1 | -2 | 4 | 6 | 113 | 101 | 1 | -4 | 12 | 6 | 23 | 22 | 7 | -1 | 5 | 7 | 152 | 140 | 2 |
| 7 | 3 | 5 | 32 | 6 | 8 | -1 | 11 | 5 | 97 | 106 | 2 | -1 | 4 | 6 | 539 | 523 | 13 | -3 | 12 | 6 | 38 | 33 | 6 | 0 | 5 | 7 | 161 | 186 | 1 |
| 2 | 4 | 5 | 20 | 21 | 19 | 0 | 11 | 5 | 28 | 2 | 8 | 0 | 4 | 6 | 65 | 59 | 5 | -2 | 12 | 6 | 129 | 128 | 2 | 1 | 5 | 7 | 145 | 139 | 2 |
| 3 | 4 | 5 | 203 | 196 | 3 | 1 | 11 | 5 | 102 | 106 | 2 | 1 | 4 | 6 | 530 | 523 | 6 | -1 | 12 | 6 | 100 | 93 | 4 | 2 | 5 | 7 | 152 | 153 | 2 |
| 4 | 4 | 5 | 248 | 242 | 2 | 2 | 11 | 5 | 100 | 100 | 1 | 2 | 4 | 6 | 102 | 101 | 2 | 0 | 12 | 6 | 91 | 89 | 2 | 3 | 5 | 7 | 106 | 104 | 2 |
| 5 | 4 | 5 | 73 | 71 | 4 | 3 | 11 | 5 | 39 | 27 | 6 | 3 | 4 | 6 | 87 | 87 | 2 | 1 | 12 | 6 | 111 | 112 | 1 | 4 | 5 | 7 | 63 | 60 | 3 |
| 4 | 4 | 5 | 158 | 171 | 3 | 4 | 11 | 5 | 83 | 84 | 3 | 4 | 4 | 6 | 103 | 99 | 3 | 2 | 12 | 6 | 90 | 89 | 3 | 5 | 5 | 7 | 174 | 176 | 3 |
| 0 | 4 | 5 | 72 | 71 | 5 | 5 | 11 | 5 | 35 | 27 | 7 | 5 | 4 | 6 | 32 | 54 | 4 | 3 | 12 | 6 | 94 | 94 | 2 | 6 | 5 | 7 | 54 | 66 | 5 |
| -1 | 4 | 5 | 180 | 196 | 3 | -4 | 12 | 5 | 52 | 55 | 4 | 6 | 4 | 6 | 72 | 60 | 2 | -4 | 13 | 6 | 131 | 128 | 3 | -4 | 6 | 7 | 105 | 107 | 2 |
| 3 | 4 | 5 | 8 | 20 | 7 | -3 | 12 | 5 | 53 | 44 | 4 | -4 | 5 | 6 | 62 | 62 | 3 | -3 | 13 | 6 | 30 | 32 | 7 | -3 | 6 | 7 | 135 | 133 | 1 |
| 4 | 4 | 5 | 58 | 63 | 2 | -2 | 12 | 5 | 86 | 81 | 2 | -3 | 5 | 6 | 27 | 8 | 12 | -2 | 13 | 6 | 28 | 16 | 5 | -2 | 6 | 7 | 171 | 160 | 1 |
| 5 | 4 | 5 | 126 | 122 | 3 | -1 | 12 | 5 | 39 | 41 | 6 | -2 | 5 | 6 | 166 | 164 | 2 | -1 | 13 | 6 | 114 | 124 | 2 | -1 | 6 | 7 | 201 | 200 | 2 |
| 6 | 4 | 5 | 46 | 42 | 5 | 0 | 12 | 5 | 31 | 3 | 7 | -1 | 5 | 6 | 301 | 282 | 3 | 0 | 13 | 6 | 104 | 105 | 3 | 0 | 6 | 7 | 198 | 195 | 1 |
| 3 | 5 | 5 | 26 | 23 | 4 | 1 | 12 | 5 | 43 | 41 | 5 | 0 | 5 | 6 | 109 | 98 | 1 | 1 | 13 | 6 | 117 | 121 | 2 | 1 | 6 | 7 | 194 | 200 | 2 |
| 4 | 5 | 5 | 50 | 47 | 3 | 2 | 12 | 5 | 82 | 81 | 2 | 1 | 5 | 6 | 291 | 282 | 4 | 2 | 13 | 6 | 26 | 25 | 4 | 2 | 6 | 7 | 177 | 150 | 3 |
| 2 | 5 | 5 | 428 | 416 | 1 | 3 | 12 | 5 | 50 | 44 | 4 | 2 | 5 | 6 | 10 | 8 | 9 | 3 | 13 | 6 | 117 | 121 | 2 | 3 | 6 | 7 | 134 | 134 | 1 |
| 1 | 5 | 5 | 126 | 136 | 2 | 4 | 12 | 5 | 56 | 54 | 3 | 3 | 5 | 6 | 68 | 62 | 1 | -3 | 13 | 6 | 103 | 105 | 3 | 4 | 6 | 7 | 103 | 107 | 2 |
| 5 | 5 | 5 | 275 | 251 | 4 | -4 | 12 | 5 | 41 | 29 | 5 | 4 | 5 | 6 | 34 | 32 | 8 | -4 | 13 | 6 | 123 | 124 | 1 | 5 | 6 | 7 | 112 | 112 | 2 |
| 4 | 5 | 5 | 120 | 136 | 4 | -3 | 13 | 5 | 31 | 22 | 5 | 5 | 5 | 6 | 83 | 73 | 4 | -3 | 13 | 6 | 27 | 14 | 8 | 6 | 6 | 7 | 46 | 35 | 6 |
| 3 | 5 | 5 | 50 | 47 | 4 | -2 | 13 | 5 | 51 | 41 | 2 | -4 | 6 | 6 | 68 | 64 | 5 | -2 | 14 | 6 | 21 | 28 | 6 | -5 | 7 | 7 | 108 | 106 | 6 |
| 4 | 5 | 5 | 47 | 23 | 3 | -1 | 13 | 5 | 72 | 71 | 5 | -3 | 6 | 6 | 64 | 48 | 5 | -1 | 14 | 6 | 56 | 46 | 10 | -4 | 7 | 7 | 88 | 81 | 2 |
| 5 | 5 | 5 | 26 | 42 | 4 | 0 | 13 | 5 | 50 | 51 | 3 | -2 | 6 | 6 | 52 | 47 | 6 | 0 | 14 | 6 | 10 | 18 | 22 | -3 | 7 | 7 | 63 | 66 | 3 |
| 2 | 5 | 5 | 46 | 42 | 4 | 1 | 13 | 5 | 33 | 33 | 5 | -1 | 6 | 6 | 112 | 107 | 2 | 1 | 14 | 6 | 53 | 49 | 5 | -2 | 7 | 7 | 82 | 81 | 2 |
| 1 | 5 | 5 | 100 | 92 | 3 | 2 | 13 | 5 | 53 | 51 | 3 | 0 | 6 | 6 | 68 | 63 | 7 | 2 | 14 | 6 | 26 | 18 | 6 | -1 | 7 | 7 | 75 | 76 | 4 |
| 6 | 5 | 5 | 65 | 62 | 4 | 3 | 13 | 5 | 71 | 72 | 1 | 1 | 6 | 6 | 172 | 175 | 4 | -3 | 14 | 6 | 47 | 49 | 4 | 0 | 7 | 7 | 258 | 286 | 1 |
| 5 | 6 | 5 | 56 | 57 | 5 | -3 | 13 | 5 | 50 | 47 | 2 | 2 | 6 | 6 | 260 | 239 | 2 | -4 | 14 | 6 | 31 | 28 | 5 | 1 | 7 | 7 | 74 | 76 | 3 |
| 4 | 6 | 5 | 95 | 97 | 2 | -4 | 14 | 5 | 33 | 22 | 3 | 3 | 6 | 6 | 168 | 175 | 2 | -3 | 14 | 6 | 37 | 40 | 6 | 2 | 7 | 7 | 85 | 81 | 2 |
| 3 | 6 | 5 | 173 | 162 | 6 | -3 | 14 | 5 | 38 | 39 | 2 | 4 | 6 | 6 | 60 | 63 | 2 | -2 | 14 | 6 | 42 | 40 | 12 | 3 | 7 | 7 | 58 | 66 | 2 |
| 2 | 6 | 5 | 224 | 223 | 4 | -2 | 14 | 5 | 41 | 39 | 6 | 5 | 6 | 6 | 113 | 147 | 6 | -1 | 15 | 6 | 42 | 68 | 6 | 4 | 7 | 7 | 84 | 81 | 2 |
| 1 | 6 | 5 | 15 | 6 | 14 | -1 | 14 | 5 | 88 | 91 | 4 | -4 | 7 | 6 | 49 | 48 | 5 | 0 | 15 | 6 | 61 | 43 | 6 | 5 | 7 | 7 | 96 | 107 | 3 |
| 0 | 6 | 5 | 223 | 222 | 2 | 0 | 14 | 5 | 43 | 41 | 3 | -3 | 7 | 6 | 67 | 63 | 5 | 1 | 15 | 6 | 42 | 40 | 5 | -5 | 8 | 7 | 49 | 42 | 5 |
| 1 | 6 | 5 | 165 | 163 | 5 | 1 | 14 | 5 | 39 | 61 | 3 | -2 | 7 | 6 | 62 | 68 | 5 | 2 | 15 | 6 | 56 | 57 | 6 | -4 | 8 | 7 | 32 | 27 | 6 |
| 2 | 6 | 5 | 100 | 98 | 4 | -3 | 15 | 5 | 41 | 41 | 4 | -1 | 7 | 6 | 124 | 120 | 1 | -2 | 15 | 6 | 51 | 52 | 5 | -3 | 8 | 7 | 90 | 93 | 3 |
| 3 | 6 | 5 | 64 | 56 | 2 | -2 | 15 | 5 | 92 | 91 | 5 | 0 | 7 | 6 | 57 | 58 | 10 | -3 | 15 | 6 | 12 | 1 | 22 | -2 | 8 | 7 | 104 | 103 | 1 |
| 4 | 6 | 5 | 61 | 62 | 4 | -1 | 15 | 5 | 35 | 39 | 9 | 1 | 7 | 6 | 188 | 193 | 5 | -2 | 15 | 6 | 52 | 52 | 7 | -1 | 8 | 7 | 72 | 74 | 1 |
| 5 | 6 | 5 | 76 | 68 | 4 | 0 | 15 | 5 | 36 | 31 | 10 | 2 | 7 | 6 | 53 | 55 | 5 | 0 | 15 | 6 | 35 | 42 | 6 | 0 | 8 | 7 | 268 | 261 | 1 |
| -4 | 7 | 5 | 24 | 64 | 23 | 1 | 15 | 5 | 74 | 80 | 14 | 3 | 7 | 6 | 134 | 123 | 3 | 1 | 15 | 6 | 224 | 211 | 3 | 1 | 8 | 7 | 98 | 105 | 1 |
| -3 | 7 | 5 | 83 | 89 | 4 | 2 | 15 | 5 | 21 | 10 | 3 | -3 | 7 | 6 | 171 | 186 | 3 | 2 | 15 | 6 | 28 | 30 | 3 | 2 | 8 | 7 | 272 | 261 | 2 |
| -2 | 7 | 5 | 47 | 47 | 2 | -2 | 16 | 5 | 45 | 51 | 2 | -4 | 7 | 6 | 130 | 123 | 2 | 0 | 15 | 6 | 108 | 111 | 5 | 3 | 8 | 7 | 76 | 74 | 1 |
| -1 | 7 | 5 | 82 | 82 | 1 | -1 | 16 | 5 | 22 | 10 | 4 | -3 | 7 | 6 | 53 | 55 | 3 | 1 | 0 | 7 | 73 | 75 | 16 | 4 | 8 | 7 | 102 | 103 | 2 |
| 3 | 7 | 5 | 173 | 177 | 2 | -2 | 16 | 5 | 75 | 80 | 1 | -2 | 7 | 6 | 189 | 193 | 1 | 2 | 0 | 7 | 17 | 1 | 5 | 5 | 8 | 7 | 91 | 93 | 2 |
| 2 | 7 | 5 | 201 | 203 | 3 | -1 | 16 | 5 | 40 | 31 | 7 | -3 | 0 | 7 | 53 | 57 | 3 | 1 | 1 | 7 | 51 | 64 | 5 | 6 | 8 | 7 | 27 | 27 | 1 |
| 1 | 7 | 5 | 343 | 344 | 27 | -2 | 16 | 5 | 26 | 10 | 2 | -1 | 0 | 7 | 118 | 120 | 2 | -1 | 1 | 7 | 135 | 132 | 2 | -4 | 8 | 7 | 53 | 31 | 9 |
| 0 | 7 | 5 | 196 | 204 | 6 | -1 | 16 | 5 | 64 | 63 | 3 | -4 | 1 | 7 | 43 | 35 | 6 | | | | | | | | | | | | | 4 |

TABLE 7-continued

Observed and calculated structure factors for 2-Mbis-P

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| 2 | 7 | 5 | 171 | 177 | 1 | -5 | 16 | 5 | 35 | 35 | 2 | -5 | 8 | 6 | 67 | 61 | 9 | -4 | 9 | 7 | 180 | 176 | 2 | -5 | 9 | 7 | 22 | 6 | 21 |
| 3 | 7 | 5 | 81 | 83 | 1 | -4 | 16 | 5 | 59 | 63 | 2 | -4 | 8 | 6 | 67 | 47 | 2 | -3 | 9 | 7 | 162 | 168 | 2 | -4 | 9 | 7 | 63 | 62 | 2 |
| 4 | 7 | 5 | 46 | 46 | 2 | -3 | 16 | 5 | 25 | 10 | 11 | -3 | 8 | 6 | 39 | 35 | 1 | -2 | 9 | 7 | 132 | 132 | 2 | -3 | 9 | 7 | 85 | 90 | 1 |
| 5 | 7 | 5 | 82 | 89 | 2 | -2 | 0 | 6 | 402 | 451 | 15 | -2 | 8 | 6 | 68 | 65 | 2 | -1 | 9 | 7 | 191 | 189 | 4 | -2 | 9 | 7 | 121 | 119 | 1 |
| 6 | 7 | 5 | 63 | 64 | 4 | -1 | 0 | 6 | 69 | 75 | 4 | -1 | 8 | 6 | 112 | 115 | 2 | 0 | 9 | 7 | 250 | 250 | 2 | -1 | 9 | 7 | 197 | 194 | 2 |
| 6 | 8 | 5 | 43 | 20 | 7 | 0 | 0 | 6 | 27 | 29 | 7 | 0 | 8 | 6 | 18 | 13 | 12 | 1 | 9 | 7 | 178 | 178 | 2 | 0 | 9 | 7 | 178 | 194 | 1 |
| 5 | 8 | 5 | 69 | 59 | 2 | 2 | 0 | 6 | 85 | 80 | 4 | 1 | 8 | 6 | 112 | 114 | 1 | 2 | 9 | 7 | 180 | 180 | 2 | 1 | 9 | 7 | 188 | 194 | 1 |
| 4 | 8 | 5 | 117 | 117 | 1 | 3 | 0 | 6 | 160 | 166 | 3 | 2 | 8 | 6 | 68 | 65 | 1 | 3 | 9 | 7 | 128 | 132 | 2 | 2 | 9 | 7 | 117 | 118 | 6 |
| 3 | 8 | 5 | 133 | 128 | 2 | 4 | 0 | 6 | 112 | 109 | 2 | 3 | 8 | 6 | 37 | 35 | 3 | 4 | 9 | 7 | 163 | 168 | 3 | 3 | 9 | 7 | 97 | 90 | 2 |
| 2 | 8 | 5 | 63 | 62 | 2 | -6 | 1 | 6 | 205 | 205 | 1 | 4 | 8 | 6 | 69 | 67 | 3 | 5 | 9 | 7 | 190 | 176 | 3 | 4 | 9 | 7 | 68 | 62 | 3 |
| 1 | 8 | 5 | 371 | 376 | 3 | -5 | 1 | 6 | 89 | 87 | 3 | 5 | 8 | 6 | 50 | 61 | 3 | -5 | 10 | 7 | 138 | 132 | 3 | -5 | 10 | 7 | 43 | 43 | 7 |
| 0 | 8 | 5 | 24 | 31 | 6 | -4 | 1 | 6 | 132 | 125 | 2 | 6 | 8 | 6 | 36 | 16 | 6 | -4 | 10 | 7 | 63 | 63 | 4 | -4 | 10 | 7 | 95 | 98 | 2 |
| 2 | 8 | 5 | 380 | 376 | 8 | -3 | 1 | 6 | 215 | 217 | 2 | -5 | 9 | 6 | 122 | 121 | 2 | -3 | 10 | 7 | 93 | 90 | 3 | -3 | 10 | 7 | 160 | 131 | 1 |
| 3 | 8 | 5 | 61 | 62 | 2 | -2 | 1 | 6 | 329 | 336 | 6 | -4 | 9 | 6 | 158 | 153 | 1 | -2 | 10 | 7 | 31 | 31 | 4 | -2 | 10 | 7 | 134 | 135 | 1 |
| 2 | 8 | 5 | 130 | 128 | 2 | -1 | 1 | 6 | 174 | 173 | 2 | -3 | 9 | 6 | 97 | 94 | 2 | -1 | 10 | 7 | 61 | 70 | 2 | -1 | 10 | 7 | 127 | 125 | 3 |
| 3 | 8 | 5 | 120 | 117 | 1 | 0 | 1 | 6 | 155 | 165 | 1 | -2 | 9 | 6 | 133 | 129 | 3 | 0 | 10 | 7 | 140 | 132 | 2 | 0 | 10 | 7 | 159 | 138 | 1 |
| 4 | 8 | 5 | 67 | 58 | 3 | 1 | 1 | 6 | 160 | 173 | 2 | -1 | 9 | 6 | 105 | 101 | 1 | 1 | 10 | 7 | 394 | 385 | 3 | 1 | 10 | 7 | 125 | 125 | 1 |
| 5 | 8 | 5 | 33 | 20 | 7 | 2 | 1 | 6 | 333 | 336 | 3 | 0 | 9 | 6 | 143 | 153 | 1 | 2 | 10 | 7 | 111 | 114 | 1 | 2 | 10 | 7 | 135 | 135 | 1 |
| 5 | 8 | 5 | 28 | 33 | 8 | 3 | 1 | 6 | 207 | 218 | 2 | 1 | 9 | 6 | 101 | 101 | 1 | 3 | 10 | 7 | 378 | 385 | 6 | 3 | 10 | 7 | 154 | 151 | 3 |
| 4 | 8 | 5 | 96 | 98 | 1 | 4 | 1 | 6 | 127 | 124 | 2 | 2 | 9 | 6 | 134 | 129 | 1 | -5 | 0 | 9 | 37 | 30 | 3 | 4 | 10 | 7 | 93 | 98 | 3 |
| 3 | 9 | 5 | 94 | 92 | 2 | 5 | 1 | 6 | 91 | 87 | 2 | 3 | 9 | 6 | 96 | 94 | 4 | -4 | 0 | 9 | 87 | 91 | 3 | -5 | 11 | 7 | 31 | 43 | 6 |
| 2 | 9 | 5 | 138 | 136 | 2 | 6 | 1 | 6 | 207 | 205 | 1 | 4 | 9 | 6 | 153 | 153 | 3 | -3 | 0 | 9 | 67 | 76 | 3 | -4 | 11 | 7 | 54 | 42 | 4 |
| 3 | 9 | 5 | 165 | 157 | 2 | -5 | 2 | 6 | 199 | 193 | 2 | -5 | 0 | 8 | 120 | 121 | 8 | -2 | 0 | 9 | 203 | 197 | 2 | -3 | 11 | 7 | 57 | 60 | 4 |
| 4 | 9 | 5 | 144 | 144 | 2 | -4 | 2 | 6 | 77 | 79 | 4 | -4 | 0 | 8 | 94 | 97 | 3 | -1 | 0 | 9 | 104 | 106 | 2 | -2 | 11 | 7 | 57 | 49 | 3 |
| 5 | 9 | 5 | 158 | 157 | 2 | -3 | 2 | 6 | 121 | 120 | 2 | -3 | 0 | 8 | 57 | 52 | 2 | 0 | 0 | 9 | 335 | 347 | 9 | -1 | 11 | 7 | 53 | 54 | 2 |
| 4 | 9 | 5 | 143 | 135 | 2 | -2 | 2 | 6 | 295 | 299 | 1 | -2 | 0 | 8 | 149 | 150 | 4 | 1 | 0 | 9 | 387 | 366 | 3 | 0 | 11 | 7 | 135 | 46 | 4 |
| 3 | 9 | 5 | 91 | 91 | 4 | -1 | 2 | 6 | 433 | 433 | 2 | -1 | 0 | 8 | 197 | 196 | 4 | 2 | 0 | 9 | 176 | 151 | 5 | 1 | 11 | 7 | 53 | 46 | 4 |
| 0 | 9 | 5 | 99 | 98 | 2 | 0 | 2 | 6 | 271 | 248 | 4 | 0 | 0 | 8 | 186 | 182 | 4 | 3 | 0 | 9 | 375 | 367 | 5 | 2 | 11 | 7 | 42 | 39 | 4 |
| 1 | 9 | 5 | 37 | 33 | 5 | 1 | 2 | 6 | 432 | 433 | 3 | 1 | 0 | 8 | 50 | 98 | 4 | 4 | 0 | 9 | 347 | 346 | 4 | 3 | 11 | 7 | 51 | 46 | 3 |
| 2 | 9 | 5 | 38 | 33 | 6 | 2 | 2 | 6 | 81 | 78 | 4 | 2 | 0 | 8 | 182 | 182 | 3 | -5 | 1 | 9 | 98 | 105 | 2 | 4 | 11 | 7 | 61 | 55 | 3 |
| 3 | 10 | 5 | 115 | 110 | 2 | -4 | 2 | 6 | 203 | 193 | 2 | 3 | 0 | 8 | 196 | 196 | 5 | -4 | 1 | 9 | 209 | 197 | 2 | 5 | 11 | 7 | 53 | 48 | 4 |
| 4 | 10 | 5 | 50 | 40 | 4 | 5 | 2 | 6 | 83 | 80 | 3 | 4 | 0 | 8 | 145 | 150 | 3 | -3 | 1 | 9 | 102 | 101 | 2 | 2 | 2 | 10 | 62 | 61 | 3 |
| 3 | 10 | 5 | 29 | 16 | 11 | 6 | 2 | 6 | 163 | 159 | 4 | 5 | 0 | 8 | 38 | 38 | 5 | -2 | 1 | 9 | 46 | 48 | 2 | 3 | 2 | 10 | 44 | 42 | 3 |
| 2 | 10 | 5 | 79 | 84 | 3 | -5 | 6 | 6 | 25 | 21 | 14 | 6 | 0 | 8 | 23 | 15 | 9 | -1 | 1 | 9 | 89 | 87 | 2 | 4 | 2 | 10 | 177 | 185 | 3 |
| 1 | 12 | 5 | 126 | 117 | 2 | -4 | 6 | 6 | 43 | 37 | 4 | -5 | 1 | 8 | 43 | 37 | 2 | 0 | 1 | 9 | 39 | 27 | 6 | 3 | 3 | 10 | 85 | 87 | 3 |
| 4 | 12 | 5 | 25 | 20 | 17 | -3 | 6 | 6 | 27 | 23 | 7 | -4 | 1 | 8 | 27 | 23 | 2 | 1 | 1 | 9 | 31 | 83 | 5 | 2 | 3 | 10 | 174 | 187 | 3 |
| 3 | 12 | 5 | 308 | 305 | 7 | -2 | 6 | 6 | 68 | 64 | 3 | -3 | 1 | 8 | 20 | 24 | 19 | 2 | 1 | 9 | 58 | 57 | 3 | 1 | 3 | 10 | 182 | 198 | 3 |
| 2 | 12 | 5 | 30 | 20 | 3 | -1 | 6 | 6 | 104 | 100 | 3 | -2 | 1 | 8 | 44 | 38 | 7 | 3 | 1 | 9 | 52 | 47 | 4 | 0 | 3 | 10 | 173 | 176 | 4 |
| 1 | 12 | 5 | 111 | 117 | 3 | 0 | 6 | 6 | 57 | 59 | 4 | -1 | 1 | 8 | 25 | 23 | 2 | 4 | 1 | 9 | 150 | 146 | 2 | -1 | 3 | 10 | 121 | 111 | 1 |
| 0 | 12 | 5 | 75 | 84 | 3 | 1 | 6 | 6 | 64 | 61 | 2 | 0 | 1 | 8 | 68 | 63 | 3 | -5 | 2 | 9 | 74 | 76 | 2 | -2 | 3 | 10 | 164 | 167 | 2 |
| 1 | 12 | 5 | 18 | 16 | 5 | 2 | 6 | 6 | 152 | 140 | 2 | 1 | 1 | 8 | 25 | 12 | 15 | -4 | 2 | 9 | 94 | 99 | 1 | -3 | 3 | 10 | 121 | 121 | 1 |
| 2 | 12 | 5 | 47 | 34 | 4 | 3 | 6 | 6 | 125 | 116 | 2 | 2 | 1 | 8 | 54 | 38 | 4 | -3 | 2 | 9 | 72 | 75 | 2 | -4 | 3 | 10 | 160 | 167 | 2 |
| 3 | 13 | 5 | 76 | 72 | 2 | 4 | 6 | 6 | 71 | 70 | 2 | 3 | 1 | 8 | 19 | 25 | 14 | -2 | 2 | 9 | 153 | 146 | 2 | -5 | 3 | 10 | 117 | 111 | 1 |
| 2 | 13 | 5 | 111 | 113 | 2 | 5 | 6 | 6 | 119 | 116 | 3 | 4 | 1 | 8 | 142 | 149 | 2 | -1 | 2 | 9 | 51 | 47 | 4 | -4 | 4 | 10 | 169 | 176 | 3 |
| 1 | 13 | 5 | 58 | 58 | 3 | 6 | 6 | 6 | 152 | 140 | 2 | -5 | 2 | 8 | 58 | 62 | 2 | 0 | 2 | 9 | 59 | 57 | 4 | -3 | 4 | 10 | 175 | 198 | 3 |
| 0 | 13 | 5 | 109 | 113 | 1 | -5 | 6 | 6 | 60 | 60 | 4 | -5 | 3 | 8 | 160 | 183 | 2 | 1 | 2 | 9 | 44 | 43 | 4 | -4 | 4 | 10 | 71 | 64 | 3 |
|  |  |  |  |  |  |  |  |  | 58 | 59 |  |  |  |  |  |  |  |  |  |  | 53 | 47 | 6 |  |  |  | 56 | 55 | 1 |

TABLE 7-continued

Observed and calculated structure factors for 2-Mbis-P

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| 2 | 13 | 7 | 75 | 72 | 2 | 5 | 6 | 8 | 49 | 41 | 5 | 5 | 0 | 9 | 103 | 105 | 2 | 144 | 146 | 2 | 43 | 40 | 2 |
| 3 | 13 | 7 | 28 | 22 | 7 | 6 | 6 | 8 | 49 | 44 | 5 | -5 | 1 | 9 | 121 | 119 | 3 | -2 | 4 | 10 | 99 | 88 | 1 |
| 4 | 13 | 7 | 34 | 34 | 6 | -4 | 7 | 8 | 80 | 83 | 1 | -4 | 1 | 9 | 56 | 51 | 3 | -1 | 4 | 10 | 328 | 328 | 8 |
| 3 | 14 | 7 | 29 | 28 | 20 | -3 | 7 | 8 | 69 | 65 | 1 | -3 | 1 | 9 | 26 | 30 | 3 | 0 | 4 | 10 | 91 | 68 | 1 |
| 2 | 14 | 7 | 36 | 30 | 10 | -2 | 7 | 8 | 60 | 58 | 2 | -2 | 1 | 9 | 84 | 81 | 2 | 1 | 4 | 10 | 39 | 40 | 1 |
| 1 | 14 | 7 | 104 | 112 | 9 | -1 | 7 | 8 | 94 | 91 | 1 | -1 | 1 | 9 | 150 | 152 | 7 | 2 | 4 | 10 | 61 | 55 | 3 |
| 0 | 14 | 7 | 36 | 35 | 8 | 0 | 7 | 8 | 88 | 90 | 1 | 0 | 1 | 9 | 179 | 191 | 6 | 3 | 4 | 10 | 63 | 64 | 3 |
| 1 | 14 | 7 | 108 | 112 | 2 | 1 | 7 | 8 | 93 | 92 | 2 | 1 | 1 | 9 | 147 | 152 | 1 | 4 | 4 | 10 | 61 | 77 | 3 |
| 2 | 14 | 7 | 28 | 30 | 6 | 2 | 7 | 8 | 62 | 59 | 3 | 2 | 1 | 9 | 80 | 81 | 2 | -4 | 5 | 10 | 168 | 170 | 3 |
| 3 | 14 | 7 | 37 | 28 | 8 | 3 | 7 | 8 | 71 | 46 | 3 | 3 | 1 | 9 | 34 | 30 | 3 | -3 | 5 | 10 | 73 | 73 | 3 |
| 2 | 14 | 7 | 56 | 59 | 9 | 4 | 7 | 8 | 78 | 82 | 3 | 4 | 1 | 9 | 47 | 51 | 3 | -2 | 5 | 10 | 121 | 118 | 2 |
| 1 | 15 | 7 | 63 | 69 | 9 | -4 | 7 | 8 | 54 | 55 | 6 | 5 | 1 | 9 | 128 | 119 | 3 | -1 | 5 | 10 | 150 | 146 | 1 |
| 0 | 15 | 7 | 94 | 88 | 2 | -3 | 7 | 8 | 67 | 54 | 4 | -5 | 2 | 9 | 51 | 41 | 5 | 0 | 5 | 10 | 75 | 75 | 1 |
| 1 | 15 | 7 | 69 | 68 | 2 | -2 | 7 | 8 | 126 | 123 | 5 | -4 | 2 | 9 | 115 | 122 | 3 | 1 | 5 | 10 | 147 | 146 | 4 |
| 2 | 15 | 7 | 56 | 59 | 2 | -1 | 7 | 8 | 120 | 116 | 2 | -3 | 2 | 9 | 31 | 30 | 2 | 2 | 5 | 10 | 115 | 118 | 3 |
| 1 | 16 | 7 | 48 | 45 | 3 | -1 | 7 | 8 | 40 | 33 | 3 | -2 | 2 | 9 | 200 | 201 | 3 | 3 | 5 | 10 | 71 | 74 | 10 |
| 0 | 16 | 7 | 34 | 31 | 4 | -1 | 8 | 8 | 147 | 141 | 2 | -1 | 2 | 9 | 284 | 274 | 2 | 4 | 5 | 10 | 147 | 170 | 3 |
| 1 | 16 | 7 | 458 | 523 | 44 | -4 | 8 | 8 | 120 | 116 | 3 | 0 | 2 | 9 | 541 | 526 | 4 | -4 | 6 | 10 | 26 | 44 | 2 |
| 0 | 0 | 8 | 55 | 59 | 1 | -3 | 8 | 8 | 36 | 33 | 4 | 1 | 2 | 9 | 273 | 275 | 2 | -3 | 6 | 10 | 69 | 66 | 2 |
| -2 | 2 | 8 | 226 | 227 | 3 | -1 | 8 | 8 | 162 | 164 | 1 | 2 | 2 | 9 | 192 | 201 | 3 | -2 | 6 | 10 | 100 | 100 | 2 |
| -3 | 3 | 8 | 116 | 115 | 1 | -4 | 8 | 8 | 30 | 32 | 3 | 3 | 2 | 9 | 21 | 30 | 5 | -1 | 6 | 10 | 41 | 38 | 2 |
| 5 | 0 | 8 | 115 | 117 | 3 | -4 | 8 | 8 | 124 | 116 | 2 | 4 | 2 | 9 | 107 | 121 | 4 | 0 | 6 | 10 | 89 | 82 | 3 |
| 6 | 0 | 8 | 41 | 51 | 2 | -3 | 8 | 8 | 144 | 141 | 2 | 5 | 2 | 9 | 85 | 78 | 2 | 1 | 6 | 10 | 198 | 187 | 2 |
| 5 | 1 | 8 | 85 | 79 | 4 | 6 | 8 | 8 | 22 | 33 | 7 | -5 | 3 | 9 | 100 | 95 | 3 | 2 | 6 | 10 | 87 | 82 | 4 |
| 3 | 1 | 8 | 178 | 174 | 3 | 5 | 8 | 8 | 116 | 123 | 2 | -4 | 3 | 9 | 103 | 105 | 1 | 3 | 6 | 10 | 37 | 38 | 1 |
| -4 | 1 | 8 | 91 | 83 | 2 | 4 | 8 | 8 | 42 | 6 | 2 | -3 | 3 | 9 | 21 | 9 | 2 | -4 | 6 | 10 | 103 | 99 | 2 |
| -2 | 1 | 8 | 65 | 68 | 7 | -4 | 9 | 8 | 97 | 96 | 2 | -2 | 3 | 9 | 233 | 217 | 10 | -3 | 7 | 10 | 66 | 67 | 2 |
| -1 | 1 | 8 | 233 | 239 | 3 | -3 | 9 | 8 | 53 | 58 | 3 | -1 | 3 | 9 | 44 | 36 | 2 | -2 | 7 | 10 | 62 | 71 | 2 |
| 0 | 1 | 8 | 407 | 410 | 2 | -2 | 9 | 8 | 132 | 126 | 3 | 0 | 3 | 9 | 220 | 217 | 3 | -1 | 7 | 10 | 73 | 68 | 2 |
| 1 | 1 | 8 | 116 | 124 | 6 | -1 | 9 | 8 | 159 | 155 | 3 | 1 | 3 | 9 | 101 | 104 | 2 | 0 | 7 | 10 | 69 | 98 | 2 |
| 2 | 1 | 8 | 394 | 410 | 3 | 0 | 9 | 8 | 174 | 173 | 2 | 2 | 3 | 9 | 123 | 123 | 5 | 1 | 7 | 10 | 99 | 98 | 2 |
| 3 | 1 | 8 | 221 | 238 | 5 | 1 | 9 | 8 | 157 | 155 | 2 | 3 | 3 | 9 | 78 | 75 | 3 | 2 | 7 | 10 | 46 | 40 | 4 |
| 4 | 1 | 8 | 70 | 69 | 2 | 2 | 9 | 8 | 131 | 126 | 3 | 4 | 3 | 9 | 105 | 107 | 1 | 3 | 7 | 10 | 48 | 47 | 2 |
| 5 | 1 | 8 | 85 | 82 | 6 | 3 | 9 | 8 | 53 | 58 | 3 | -5 | 4 | 9 | 62 | 70 | 6 | -4 | 7 | 10 | 41 | 40 | 4 |
| 6 | 1 | 8 | 181 | 173 | 3 | -5 | 10 | 8 | 94 | 96 | 4 | -4 | 4 | 9 | 110 | 111 | 1 | -3 | 7 | 10 | 103 | 98 | 3 |
| 5 | 2 | 8 | 82 | 74 | 4 | -4 | 10 | 8 | 24 | 37 | 7 | -3 | 4 | 9 | 269 | 269 | 2 | -2 | 7 | 10 | 62 | 68 | 3 |
| 4 | 2 | 8 | 35 | 37 | 5 | -3 | 10 | 8 | 35 | 66 | 3 | -2 | 4 | 9 | 132 | 129 | 2 | -1 | 7 | 10 | 66 | 71 | 3 |
| 3 | 2 | 8 | 71 | 74 | 2 | -2 | 10 | 8 | 71 | 44 | 4 | -1 | 4 | 9 | 253 | 231 | 2 | 0 | 7 | 10 | 36 | 46 | 7 |
| 2 | 2 | 8 | 42 | 40 | 7 | -1 | 10 | 8 | 33 | 20 | 4 | 0 | 4 | 9 | 126 | 128 | 1 | 1 | 8 | 10 | 64 | 64 | 4 |
| 1 | 2 | 8 | 214 | 231 | 2 | 0 | 10 | 8 | 112 | 117 | 2 | 1 | 4 | 9 | 252 | 269 | 2 | 2 | 8 | 10 | 50 | 45 | 3 |
| 0 | 2 | 8 | 120 | 121 | 3 | 1 | 10 | 8 | 136 | 138 | 4 | 2 | 4 | 9 | 114 | 111 | 4 | 3 | 8 | 10 | 103 | 109 | 1 |
| 1 | 2 | 8 | 130 | 126 | 3 | 2 | 10 | 8 | 126 | 122 | 2 | 3 | 4 | 9 | 57 | 70 | 2 | -3 | 8 | 10 | 43 | 44 | 1 |
| 2 | 2 | 8 | 172 | 160 | 4 | -3 | 11 | 8 | 133 | 136 | 4 | 4 | 4 | 9 | 84 | 62 | 2 | -1 | 8 | 10 | 92 | 89 | 3 |
| 1 | 2 | 8 | 124 | 121 | 1 | -2 | 11 | 8 | 115 | 113 | 3 | 5 | 4 | 9 | 28 | 20 | 3 | 1 | 8 | 10 | 46 | 44 | 3 |
| 0 | 2 | 8 | 109 | 121 | 1 | -1 | 11 | 8 | 53 | 58 | 4 | -5 | 5 | 9 | 84 | 83 | 3 | 2 | 8 | 10 | 101 | 105 | 3 |
| 3 | 2 | 8 | 219 | 231 | 2 | 0 | 11 | 8 | 94 | 96 | 4 | -3 | 5 | 9 | 82 | 88 | 1 | 3 | 8 | 10 | 46 | 45 | 4 |
| 4 | 2 | 8 | 38 | 40 | 2 | 1 | 11 | 8 | 27 | 21 | 5 | -4 | 5 | 9 | 66 | 72 | 3 | 3 | 8 | 10 | 46 | 45 | 4 |

TABLE 7-continued

Observed and calculated structure factors for 2-Mbis-P

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| 5 | 2 | 8 | 46 | 37 | 4 | -2 | 5 | 9 | 21 | 10 | 20 | -1 | 14 | 9 | 85 | 82 | 2 | 4 | 8 | 10 | 57 | 64 | 4 |
| 6 | 3 | 8 | 80 | 52 | 3 | -1 | 5 | 9 | 123 | 123 | 3 | 0 | 14 | 9 | 90 | 90 | 2 | 5 | 8 | 10 | 54 | 62 | 5 |
| 3 | 3 | 8 | 161 | 164 | 2 | 0 | 5 | 9 | 105 | 105 | 1 | 1 | 14 | 9 | 66 | 72 | 2 | -4 | 9 | 10 | 71 | 73 | 3 |
| 2 | 3 | 8 | 80 | 80 | 3 | 1 | 5 | 9 | 130 | 129 | 3 | -2 | 0 | 10 | 95 | 90 | 2 | -3 | 9 | 10 | 77 | 75 | 1 |
| 1 | 3 | 8 | 492 | 476 | 4 | 2 | 5 | 9 | 34 | 1 | 5 | -1 | 0 | 10 | 84 | 82 | 4 | -2 | 9 | 10 | 30 | 30 | 6 |
| 0 | 3 | 8 | 44 | 42 | 2 | 3 | 5 | 9 | 128 | 129 | 5 | 1 | 0 | 10 | 88 | 88 | 2 | -1 | 9 | 10 | 64 | 62 | 2 |
| -1 | 3 | 8 | 486 | 476 | 10 | 4 | 5 | 9 | 100 | 105 | 2 | 2 | 0 | 10 | 81 | 83 | 2 | 0 | 9 | 10 | 45 | 45 | 2 |
| -2 | 3 | 8 | 78 | 81 | 2 | 5 | 5 | 9 | 121 | 123 | 2 | -4 | 1 | 10 | 40 | 48 | 5 | 1 | 9 | 10 | 64 | 62 | 3 |
| 1 | 3 | 8 | 160 | 165 | 7 | 6 | 5 | 9 | 27 | 10 | 6 | -3 | 1 | 10 | 109 | 107 | 2 | 2 | 9 | 10 | 27 | 30 | 7 |
| 2 | 3 | 8 | 84 | 85 | 1 | -4 | 6 | 9 | 12 | 22 | 4 | -2 | 1 | 10 | 31 | 36 | 2 | 3 | 9 | 10 | 78 | 75 | 3 |
| 3 | 3 | 8 | 64 | 59 | 3 | -3 | 6 | 9 | 87 | 84 | 2 | -1 | 1 | 10 | 121 | 121 | 4 | 4 | 9 | 10 | 71 | 73 | 4 |
| 4 | 3 | 8 | 66 | 60 | 5 | -2 | 6 | 9 | 32 | 24 | 16 | 0 | 1 | 10 | 105 | 110 | 2 | -4 | 10 | 10 | 49 | 57 | 7 |
| 5 | 3 | 8 | 133 | 122 | 2 | -1 | 6 | 9 | 79 | 81 | 3 | 1 | 1 | 10 | 26 | 20 | 2 | -3 | 10 | 10 | 47 | 43 | 3 |
| 6 | 3 | 8 | 182 | 179 | 1 | 0 | 6 | 9 | 242 | 234 | 1 | 2 | 1 | 10 | 104 | 110 | 3 | -2 | 10 | 10 | 29 | 35 | 4 |
| 3 | 4 | 8 | 77 | 64 | 5 | 1 | 6 | 9 | 79 | 82 | 7 | 3 | 1 | 10 | 123 | 122 | 1 | -1 | 10 | 10 | 137 | 135 | 1 |
| 2 | 4 | 8 | 60 | 66 | 2 | 2 | 6 | 9 | 24 | 24 | 5 | -4 | 2 | 10 | 35 | 36 | 2 | 0 | 10 | 10 | 114 | 108 | 4 |
| 0 | 4 | 8 | 75 | 64 | 3 | 3 | 6 | 9 | 82 | 84 | 4 | -3 | 2 | 10 | 105 | 107 | 2 | 1 | 10 | 10 | 361 | 371 | 2 |
| 1 | 4 | 8 | 131 | 122 | 6 | 4 | 6 | 9 | 33 | 22 | 5 | -2 | 2 | 10 | 61 | 68 | 6 | 2 | 10 | 10 | 114 | 108 | 3 |
| 2 | 4 | 8 | 92 | 99 | 4 | 5 | 6 | 9 | 39 | 30 | 7 | -1 | 2 | 10 | 19 | 49 | 6 | 3 | 10 | 10 | 138 | 134 | 11 |
| 3 | 4 | 8 | 77 | 68 | 3 | 6 | 6 | 9 | 96 | 96 | 2 | 0 | 2 | 10 | 86 | 87 | 3 | 4 | 10 | 10 | 24 | 35 | 9 |
| 4 | 4 | 8 | 73 | 71 | 4 | -4 | 7 | 9 | 50 | 47 | 5 | 1 | 2 | 10 | 94 | 94 | 1 | -4 | 11 | 10 | 32 | 43 | 3 |
| 5 | 4 | 8 | 42 | 38 | 2 | -3 | 7 | 9 | 57 | 45 | 3 | 2 | 2 | 10 | 148 | 151 | 2 | -3 | 11 | 10 | 59 | 58 | 2 |
| 6 | 4 | 8 | 25 | 21 | 6 | -2 | 7 | 9 | 46 | 47 | 4 | -4 | 3 | 10 | 52 | 55 | 4 | -2 | 11 | 10 | 116 | 120 | 1 |
| 3 | 5 | 8 | 161 | 158 | 1 | -1 | 7 | 9 | 99 | 96 | 3 | -3 | 3 | 10 | 90 | 87 | 3 | -1 | 11 | 10 | 74 | 82 | 4 |
| 2 | 5 | 8 | 136 | 135 | 2 | 0 | 7 | 9 | 33 | 30 | 2 | -2 | 3 | 10 | 52 | 55 | 2 | 0 | 11 | 10 | 144 | 144 | 3 |
| 1 | 5 | 8 | 71 | 70 | 4 | 1 | 7 | 9 | 27 | 24 | 7 | -1 | 3 | 10 | 155 | 151 | 3 | 1 | 11 | 10 | 189 | 187 | 5 |
| 0 | 5 | 8 | 129 | 134 | 2 | 2 | 7 | 9 | 24 | 25 | 5 | 0 | 3 | 10 | 95 | 35 | 2 | 2 | 11 | 10 | 143 | 144 | 1 |
| -1 | 5 | 8 | 68 | 81 | 2 | 3 | 7 | 9 | 60 | 74 | 8 | 1 | 3 | 10 | 114 | 111 | 16 | 3 | 11 | 10 | 21 | 18 | 5 |
| 11 | 11 | 8 | 115 | 120 | 3 | 4 | 7 | 9 | 33 | 24 | 4 | 2 | 3 | 10 | 62 | 62 | 6 | 4 | 11 | 10 | 80 | 80 | 1 |
| 11 | 11 | 10 | 59 | 58 | 3 | -4 | 8 | 9 | 130 | 131 | 5 | -4 | 4 | 10 | 57 | 60 | 2 | -4 | 12 | 10 | 110 | 107 | 3 |
| 4 | 12 | 10 | 28 | 42 | 2 | -3 | 8 | 9 | 27 | 22 | 2 | -3 | 4 | 10 | 44 | 50 | 10 | -3 | 12 | 10 | 100 | 96 | 5 |
| 3 | 12 | 10 | 31 | 37 | 3 | -2 | 8 | 9 | 84 | 82 | 2 | -2 | 4 | 10 | 93 | 92 | 9 | -2 | 12 | 10 | 56 | 65 | 3 |
| 2 | 12 | 10 | 76 | 78 | 1 | -1 | 8 | 9 | 34 | 23 | 8 | -1 | 4 | 10 | 33 | 27 | 4 | -1 | 12 | 10 | 25 | 39 | 5 |
| 1 | 12 | 10 | 100 | 97 | 2 | 0 | 8 | 9 | 85 | 82 | 6 | 0 | 4 | 10 | 67 | 65 | 2 | 0 | 12 | 10 | 45 | 44 | 11 |
| 0 | 12 | 10 | 59 | 57 | 4 | 1 | 8 | 9 | 23 | 23 | 4 | 1 | 4 | 10 | 100 | 101 | 5 | 1 | 12 | 10 | 53 | 50 | 18 |
| -1 | 12 | 10 | 97 | 98 | 7 | 2 | 8 | 9 | 136 | 131 | 2 | 2 | 4 | 10 | 227 | 236 | 3 | 2 | 12 | 10 | 45 | 44 | 3 |
| -2 | 12 | 10 | 72 | 78 | 5 | 3 | 8 | 9 | 34 | 24 | 7 | 3 | 4 | 10 | 103 | 103 | 3 | 3 | 12 | 10 | 88 | 88 | 1 |
| -3 | 12 | 10 | 31 | 37 | 4 | 4 | 8 | 9 | 40 | 54 | 2 | -4 | 5 | 10 | 63 | 65 | 4 | 4 | 12 | 10 | 222 | 221 | 1 |
| 4 | 13 | 10 | 76 | 42 | 5 | -4 | 9 | 9 | 39 | 37 | 4 | -3 | 5 | 10 | 24 | 27 | 3 | -4 | 13 | 10 | 87 | 88 | 2 |
| 3 | 13 | 10 | 56 | 26 | 6 | -3 | 9 | 9 | 34 | 34 | 8 | -2 | 5 | 10 | 88 | 92 | 8 | -3 | 13 | 10 | 80 | 88 | 6 |
| 2 | 13 | 10 | 24 | 39 | 4 | -2 | 9 | 9 | 45 | 41 | 2 | -1 | 5 | 10 | 89 | 104 | 8 | -2 | 13 | 10 | 48 | 51 | 6 |
| 1 | 13 | 10 | 34 | 51 | 2 | -1 | 9 | 9 | 184 | 185 | 1 | 0 | 5 | 10 | 59 | 64 | 9 | -1 | 13 | 10 | 45 | 44 | 3 |
| 0 | 13 | 10 | 59 | 51 | 4 | 0 | 9 | 9 | 34 | 31 | 1 | 1 | 5 | 10 | 81 | 82 | 8 | 0 | 13 | 10 | 54 | 42 | 7 |
| -1 | 13 | 10 | 50 | 51 | 2 | 1 | 9 | 9 | 186 | 185 | 2 | 2 | 5 | 10 | 66 | 63 | 9 | 1 | 13 | 10 | 66 | 69 | 2 |
| -2 | 13 | 10 | 28 | 40 | 8 | 2 | 9 | 9 | 40 | 41 | 1 | 3 | 5 | 10 | 66 | 67 | 3 | 2 | 13 | 10 | 48 | 52 | 2 |
| -3 | 13 | 10 | 24 | 26 | 23 | 3 | 9 | 9 | 17 | 34 | 16 | 4 | 5 | 10 | 59 | 63 | 1 | 3 | 13 | 10 | 30 | 21 | 8 |

TABLE 7-continued

Observed and calculated structure factors for 2-Mbis-P

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| 2 | 14 | 10 | 36 | 30 | 4 | 4 | 8 | 11 | 45 | 37 | 6 | 1 | 4 | 12 | 70 | 67 | 1 | 0 | 9 | 13 | 98 | 95 | 1 |
| 1 | 14 | 10 | 48 | 52 | 3 | 5 | 8 | 11 | 20 | 27 | 20 | 2 | 4 | 12 | 64 | 63 | 3 | 1 | 9 | 13 | 34 | 21 | 5 |
| 0 | 14 | 10 | 56 | 55 | 3 | -4 | 9 | 11 | 42 | 45 | 11 | 2 | 4 | 12 | 79 | 82 | 2 | 2 | 9 | 13 | 53 | 52 | 3 |
| -1 | 14 | 10 | 39 | 52 | 7 | -3 | 9 | 11 | 122 | 123 | 1 | 3 | 4 | 12 | 51 | 64 | 4 | 3 | 9 | 13 | 62 | 69 | 5 |
| 2 | 14 | 10 | 39 | 30 | 5 | -2 | 9 | 11 | 88 | 86 | 1 | 4 | 4 | 12 | 28 | 41 | 10 | 4 | 9 | 13 | 38 | 42 | 7 |
| 2 | 15 | 10 | 27 | 18 | 6 | -1 | 9 | 11 | 145 | 144 | 1 | -4 | 5 | 12 | 78 | 90 | 8 | -4 | 10 | 13 | 50 | 53 | 4 |
| 1 | 15 | 10 | 29 | 39 | 13 | 0 | 9 | 11 | 41 | 42 | 2 | -3 | 5 | 12 | 30 | 33 | 2 | -3 | 10 | 13 | 70 | 76 | 3 |
| 0 | 15 | 10 | 76 | 85 | 2 | 1 | 9 | 11 | 141 | 144 | 1 | -2 | 5 | 12 | 115 | 116 | 1 | -2 | 10 | 13 | 37 | 30 | 3 |
| -1 | 0 | 11 | 48 | 59 | 2 | 2 | 9 | 11 | 88 | 86 | 4 | -1 | 5 | 12 | 32 | 29 | 2 | -1 | 10 | 13 | 76 | 76 | 3 |
| 2 | 0 | 11 | 189 | 196 | 2 | 3 | 9 | 11 | 129 | 123 | 3 | 0 | 5 | 12 | 135 | 139 | 1 | 0 | 10 | 13 | 101 | 102 | 1 |
| 3 | 0 | 11 | 89 | 91 | 2 | 4 | 9 | 11 | 43 | 45 | 6 | 1 | 5 | 12 | 38 | 29 | 2 | 1 | 10 | 13 | 72 | 74 | 2 |
| 4 | 0 | 11 | 95 | 94 | 3 | -4 | 10 | 11 | 31 | 34 | 13 | 2 | 5 | 12 | 112 | 116 | 1 | 2 | 10 | 13 | 27 | 30 | 8 |
| -4 | 1 | 11 | 158 | 159 | 2 | -3 | 10 | 11 | 85 | 81 | 1 | 3 | 5 | 12 | 30 | 33 | 2 | 3 | 10 | 13 | 63 | 76 | 3 |
| -3 | 1 | 11 | 64 | 61 | 4 | -2 | 10 | 11 | 116 | 109 | 2 | 4 | 5 | 12 | 81 | 90 | 2 | 4 | 10 | 13 | 51 | 53 | 5 |
| -2 | 1 | 11 | 199 | 192 | 2 | -1 | 10 | 11 | 32 | 33 | 4 | -5 | 6 | 12 | 16 | 35 | 16 | -3 | 11 | 13 | 21 | 19 | 20 |
| -1 | 1 | 11 | 50 | 42 | 4 | 0 | 10 | 11 | 303 | 302 | 2 | -4 | 6 | 12 | 92 | 91 | 4 | -2 | 11 | 13 | 100 | 99 | 1 |
| 0 | 1 | 11 | 194 | 192 | 2 | 1 | 10 | 11 | 36 | 33 | 4 | -3 | 6 | 12 | 42 | 45 | 2 | -1 | 11 | 13 | 32 | 30 | 3 |
| 1 | 1 | 11 | 68 | 60 | 6 | 2 | 10 | 11 | 112 | 110 | 1 | -2 | 6 | 12 | 38 | 33 | 3 | 0 | 11 | 13 | 90 | 85 | 2 |
| 2 | 1 | 11 | 155 | 158 | 4 | 3 | 10 | 11 | 77 | 80 | 2 | -1 | 6 | 12 | 85 | 86 | 2 | 1 | 11 | 13 | 38 | 30 | 4 |
| 3 | 1 | 11 | 92 | 94 | 3 | -4 | 11 | 11 | 35 | 34 | 7 | 0 | 6 | 12 | 116 | 120 | 1 | 2 | 11 | 13 | 102 | 98 | 2 |
| 4 | 1 | 11 | 100 | 104 | 2 | -3 | 11 | 11 | 43 | 48 | 6 | 1 | 6 | 12 | 86 | 85 | 2 | 3 | 11 | 13 | 25 | 19 | 11 |
| -4 | 2 | 11 | 23 | 14 | 10 | -2 | 11 | 11 | 40 | 42 | 2 | 2 | 6 | 12 | 33 | 34 | 3 | -2 | 12 | 13 | 25 | 24 | 6 |
| -3 | 2 | 11 | 98 | 95 | 2 | -1 | 11 | 11 | 70 | 67 | 4 | 3 | 6 | 12 | 50 | 45 | 2 | -1 | 12 | 13 | 35 | 35 | 3 |
| -2 | 2 | 11 | 279 | 296 | 1 | 0 | 11 | 11 | 107 | 103 | 1 | -4 | 7 | 12 | 87 | 91 | 11 | 0 | 12 | 13 | 86 | 90 | 2 |
| -1 | 2 | 11 | 183 | 186 | 1 | 1 | 11 | 11 | 24 | 4 | 25 | -3 | 7 | 12 | 13 | 30 | 3 | 1 | 12 | 13 | 29 | 35 | 5 |
| 0 | 2 | 11 | 287 | 296 | 1 | 2 | 11 | 11 | 104 | 103 | 5 | -2 | 7 | 12 | 54 | 48 | 21 | 2 | 12 | 13 | 15 | 24 | 20 |
| 1 | 2 | 11 | 97 | 95 | 3 | -3 | 12 | 11 | 66 | 67 | 3 | -1 | 7 | 12 | 81 | 78 | 6 | 3 | 12 | 13 | 40 | 33 | 14 |
| 2 | 2 | 11 | 17 | 15 | 5 | -2 | 12 | 11 | 33 | 42 | 10 | 0 | 7 | 12 | 162 | 158 | 3 | -1 | 13 | 13 | 48 | 40 | 6 |
| 3 | 2 | 11 | 102 | 104 | 5 | -1 | 12 | 11 | 39 | 47 | 2 | 1 | 7 | 12 | 110 | 108 | 10 | 0 | 13 | 13 | 24 | 33 | 3 |
| 4 | 2 | 11 | 74 | 74 | 2 | 0 | 12 | 11 | 25 | 18 | 18 | 2 | 7 | 12 | 65 | 66 | 4 | 1 | 13 | 13 | 41 | 50 | 4 |
| -4 | 3 | 11 | 117 | 117 | 4 | 1 | 12 | 11 | 76 | 77 | 6 | -5 | 8 | 12 | 111 | 108 | 6 | -3 | 0 | 14 | 92 | 95 | 1 |
| -3 | 3 | 11 | 46 | 48 | 3 | 2 | 12 | 11 | 22 | 18 | 6 | -4 | 8 | 12 | 25 | 32 | 6 | -2 | 0 | 14 | 78 | 71 | 2 |
| -2 | 3 | 11 | 23 | 29 | 3 | -3 | 13 | 11 | 49 | 56 | 4 | -3 | 8 | 12 | 68 | 72 | 8 | -1 | 0 | 14 | 118 | 114 | 8 |
| -1 | 3 | 11 | 128 | 145 | 3 | -2 | 13 | 11 | 53 | 55 | 6 | -2 | 8 | 12 | 71 | 67 | 3 | 0 | 0 | 14 | 119 | 124 | 1 |
| 0 | 3 | 11 | 25 | 20 | 3 | -1 | 13 | 11 | 27 | 20 | 6 | -1 | 8 | 12 | 87 | 84 | 1 | -5 | 1 | 14 | 102 | 97 | 10 |
| 1 | 3 | 11 | 47 | 47 | 2 | 0 | 13 | 11 | 50 | 40 | 8 | 0 | 8 | 12 | 90 | 89 | 1 | -4 | 1 | 14 | 43 | 71 | 4 |
| 2 | 3 | 11 | 112 | 117 | 3 | 1 | 13 | 11 | 34 | 20 | 12 | 1 | 8 | 12 | 88 | 89 | 1 | -3 | 1 | 14 | 31 | 29 | 1 |
| 3 | 3 | 11 | 73 | 74 | 3 | -3 | 13 | 11 | 40 | 55 | 7 | 2 | 8 | 12 | 85 | 84 | 2 | -2 | 1 | 14 | 36 | 44 | 2 |
| -4 | 4 | 11 | 45 | 52 | 5 | -2 | 14 | 11 | 55 | 56 | 7 | -4 | 9 | 12 | 72 | 67 | 4 | -1 | 1 | 14 | 35 | 33 | 4 |
| -3 | 4 | 11 | 65 | 66 | 3 | -1 | 14 | 11 | 25 | 13 | 10 | -3 | 9 | 12 | 66 | 72 | 5 | 0 | 1 | 14 | 23 | 4 | 2 |
| -2 | 4 | 11 | 189 | 186 | 3 | 0 | 14 | 11 | 26 | 28 | 4 | -2 | 9 | 12 | 13 | 36 | 12 | 1 | 1 | 14 | 50 | 60 | 1 |
| -1 | 4 | 11 | 26 | 24 | 3 | -1 | 0 | 11 | 36 | 41 | 5 | -3 | 9 | 12 | 84 | 92 | 2 | -2 | 1 | 14 | 85 | 81 | 3 |
| 1 | 4 | 11 | 79 | 83 | 3 | | | | | | | | | | | | | -1 | 1 | 14 | 57 | 61 | 1 |
| 2 | 4 | 11 | 101 | 100 | 3 | | | | | | | | | | | | | 0 | 1 | 14 | 22 | 7 | 3 |
| -1 | 4 | 11 | 26 | 24 | 5 | | | | | | | | | | | | | 1 | 1 | 14 | 38 | 33 | 5 |
| | | | | | | | | | | | | | | | | | | 2 | 1 | 14 | 38 | 44 | 4 |

TABLE 7-continued

Observed and calculated structure factors for 2-Mbis-P

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| 3 | 4 | 11 | 185 | 286 | 3 | 1 | 14 | 11 | 18 | 28 | 17 | -3 | 9 | 12 | 113 | 114 | 2 | 5 | 1 | 14 | 4 | 28 | 4 |
| 4 | 4 | 11 | 63 | 66 | 3 | 2 | 14 | 11 | 27 | 14 | 7 | -2 | 9 | 12 | 21 | 25 | 4 | -5 | 1 | 14 | 76 | 84 | 4 |
| 4 | 5 | 11 | 47 | 52 | 5 | 0 | 0 | 12 | 640 | 627 | 11 | -1 | 9 | 12 | 112 | 107 | 2 | -4 | 2 | 14 | 75 | 78 | 2 |
| 5 | 4 | 11 | 17 | 12 | 8 | 0 | 1 | 12 | 27 | 27 | 2 | 0 | 9 | 12 | 58 | 52 | 1 | -3 | 2 | 14 | 215 | 215 | 7 |
| 4 | 5 | 11 | 106 | 101 | 4 | 1 | 0 | 12 | 153 | 135 | 1 | 1 | 9 | 12 | 109 | 107 | 6 | -2 | 2 | 14 | 79 | 79 | 2 |
| 2 | 5 | 11 | 98 | 100 | 1 | 3 | 0 | 12 | 93 | 99 | 1 | 2 | 9 | 12 | 20 | 25 | 3 | -1 | 2 | 14 | 152 | 146 | 1 |
| 3 | 5 | 11 | 136 | 133 | 2 | 4 | 1 | 12 | 110 | 113 | 2 | 3 | 9 | 12 | 107 | 114 | 6 | 0 | 1 | 14 | 19 | 1 | 4 |
| 1 | 5 | 11 | 78 | 75 | 1 | -4 | 1 | 12 | 191 | 207 | 1 | 4 | 9 | 12 | 84 | 92 | 5 | 1 | 2 | 14 | 151 | 146 | 3 |
| 0 | 5 | 11 | 134 | 133 | 2 | -3 | 1 | 12 | 150 | 158 | 2 | -4 | 10 | 12 | 26 | 25 | 8 | 2 | 2 | 14 | 84 | 79 | 2 |
| -1 | 5 | 11 | 94 | 101 | 2 | -2 | 1 | 12 | 42 | 37 | 2 | -3 | 10 | 12 | 33 | 13 | 5 | 3 | 2 | 14 | 222 | 215 | 1 |
| -2 | 5 | 11 | 105 | 101 | 2 | -1 | 1 | 12 | 132 | 137 | 2 | -2 | 10 | 12 | 71 | 68 | 1 | 2 | 2 | 14 | 73 | 78 | 2 |
| -3 | 5 | 11 | 30 | 12 | 6 | 0 | 1 | 12 | 130 | 121 | 3 | -1 | 10 | 12 | 72 | 71 | 3 | 4 | 2 | 14 | 54 | 84 | 5 |
| 3 | 4 | 11 | 46 | 42 | 6 | 1 | 1 | 12 | 131 | 137 | 1 | 0 | 10 | 12 | 161 | 162 | 2 | -5 | 3 | 14 | 52 | 44 | 6 |
| 4 | 4 | 11 | 74 | 73 | 3 | 2 | 1 | 12 | 38 | 37 | 3 | 1 | 10 | 12 | 70 | 71 | 2 | -4 | 3 | 14 | 33 | 39 | 5 |
| 4 | 5 | 11 | 63 | 60 | 1 | 3 | 1 | 12 | 145 | 157 | 4 | 2 | 10 | 12 | 71 | 69 | 2 | -3 | 3 | 14 | 49 | 48 | 3 |
| 3 | 6 | 11 | 34 | 33 | 1 | 4 | 1 | 12 | 197 | 207 | 3 | 3 | 10 | 12 | 15 | 13 | 15 | -2 | 3 | 14 | 57 | 50 | 1 |
| 2 | 6 | 11 | 141 | 145 | 3 | -4 | 2 | 12 | 60 | 60 | 2 | 4 | 10 | 12 | 24 | 25 | 14 | -1 | 3 | 14 | 83 | 81 | 3 |
| -1 | 6 | 11 | 47 | 30 | 3 | -3 | 2 | 12 | 60 | 61 | 1 | -3 | 11 | 12 | 32 | 17 | 9 | 0 | 3 | 14 | 63 | 65 | 1 |
| -2 | 6 | 11 | 142 | 145 | 3 | -2 | 2 | 12 | 115 | 112 | 2 | -2 | 11 | 12 | 46 | 48 | 5 | 1 | 3 | 14 | 84 | 82 | 3 |
| -1 | 6 | 11 | 32 | 33 | 2 | -1 | 2 | 12 | 192 | 198 | 1 | -1 | 11 | 12 | 56 | 51 | 3 | 2 | 3 | 14 | 54 | 50 | 1 |
| -2 | 6 | 11 | 60 | 60 | 3 | 0 | 2 | 12 | 104 | 106 | 2 | 0 | 11 | 12 | 35 | 26 | 3 | 3 | 3 | 14 | 53 | 48 | 2 |
| -3 | 6 | 11 | 66 | 72 | 4 | 1 | 2 | 12 | 195 | 198 | 1 | 1 | 11 | 12 | 48 | 51 | 4 | 4 | 3 | 14 | 31 | 39 | 4 |
| 3 | 4 | 14 | 26 | 44 | 2 | 2 | 2 | 12 | 160 | 151 | 2 | 2 | 11 | 12 | 25 | 20 | 6 | -4 | 4 | 14 | 129 | 120 | 2 |
| 5 | 5 | 14 | 46 | 22 | 11 | 3 | 2 | 12 | 136 | 131 | 3 | 3 | 11 | 12 | 6 | 38 | 5 | -3 | 4 | 14 | 197 | 195 | 2 |
| 5 | 4 | 14 | 23 | 12 | 6 | -4 | 3 | 12 | 49 | 57 | 2 | -1 | 12 | 12 | 35 | 41 | 6 | -2 | 4 | 14 | 23 | 20 | 11 |
| 4 | 5 | 14 | 54 | 43 | 8 | -3 | 3 | 12 | 35 | 56 | 4 | 0 | 12 | 12 | 42 | 42 | 7 | -1 | 4 | 14 | 48 | 50 | 4 |
| 3 | 5 | 14 | 34 | 19 | 5 | -2 | 3 | 12 | 47 | 35 | 1 | 1 | 12 | 12 | 27 | 8 | 9 | 0 | 4 | 14 | 44 | 41 | 2 |
| 2 | 4 | 14 | 49 | 46 | 3 | -1 | 3 | 12 | 38 | 37 | 2 | 2 | 12 | 12 | 70 | 62 | 5 | 1 | 4 | 14 | 88 | 80 | 2 |
| 1 | 4 | 14 | 54 | 52 | 3 | 0 | 3 | 12 | 42 | 46 | 3 | 3 | 12 | 12 | 31 | 18 | 12 | 2 | 4 | 14 | 52 | 49 | 2 |
| 0 | 4 | 14 | 53 | 46 | 1 | 1 | 3 | 12 | 170 | 165 | 2 | -4 | 0 | 16 | 91 | 95 | 5 | 3 | 4 | 14 | 26 | 23 | 4 |
| -1 | 4 | 14 | 28 | 19 | 7 | 2 | 3 | 12 | 166 | 157 | 2 | -3 | 0 | 16 | 13 | 12 | 17 | 4 | 4 | 14 | 83 | 80 | 2 |
| -2 | 4 | 14 | 45 | 43 | 2 | 3 | 3 | 12 | 172 | 165 | 3 | -2 | 0 | 16 | 60 | 73 | 7 | -4 | 5 | 14 | 40 | 41 | 6 |
| -3 | 4 | 14 | 31 | 21 | 3 | -4 | 4 | 12 | 41 | 37 | 4 | -1 | 0 | 16 | 64 | 62 | 5 | -3 | 5 | 14 | 33 | 50 | 6 |
| 3 | 4 | 14 | 33 | 43 | 5 | -3 | 4 | 12 | 33 | 36 | 5 | 0 | 0 | 16 | 133 | 123 | 3 | -2 | 5 | 14 | 34 | 39 | 14 |
| 4 | 5 | 14 | 59 | 49 | 3 | -2 | 4 | 12 | 38 | 46 | 5 | 1 | 0 | 16 | 105 | 101 | 2 | -1 | 5 | 14 | 17 | 3 | 1 |
| 2 | 5 | 14 | 29 | 23 | 2 | -1 | 4 | 12 | 45 | 37 | 4 | 2 | 0 | 16 | 32 | 20 | 15 | 0 | 5 | 14 | 135 | 126 | 2 |
| 1 | 5 | 14 | 52 | 50 | 2 | 0 | 4 | 12 | 60 | 57 | 5 | -4 | 1 | 16 | 109 | 101 | 5 | 1 | 5 | 14 | 54 | 47 | 2 |
| 0 | 5 | 14 | 27 | 30 | 4 | 1 | 4 | 12 | 39 | 45 | 3 | -3 | 1 | 16 | 131 | 123 | 1 | 2 | 5 | 14 | 23 | 20 | 6 |
| -1 | 5 | 14 | 37 | 23 | 1 | 2 | 4 | 12 | 47 | 36 | 2 | -2 | 1 | 16 | 60 | 62 | 6 | 3 | 5 | 14 | 52 | 47 | 2 |
| -2 | 5 | 14 | 57 | 50 | 11 | 3 | 4 | 12 | 145 | 131 | 1 | -1 | 1 | 16 | 71 | 73 | 1 | 4 | 5 | 14 | 137 | 126 | 3 |
| -3 | 5 | 14 | 56 | 42 | 3 | -3 | 5 | 12 | 75 | 75 | 2 | 0 | 1 | 16 | 55 | 59 | 2 | -4 | 6 | 14 | 19 | 3 | 19 |
| 2 | 4 | 14 | 40 | 57 | 6 | -2 | 5 | 12 | 180 | 165 | 5 | 1 | 1 | 16 | 64 | 58 | 5 | -3 | 6 | 14 | 20 | 39 | 20 |
| 3 | 6 | 14 | 58 | 57 | 2 | -1 | 5 | 12 | 78 | 74 | 2 | 2 | 1 | 16 | 69 | 61 | 7 | -2 | 6 | 14 | 43 | 29 | 7 |
| 2 | 6 | 14 | 97 | 96 | 3 | 0 | 5 | 12 | 133 | 131 | 1 | 3 | 1 | 16 | 152 | 147 | 4 | -1 | 6 | 14 | 25 | 5 | 6 |
| 1 | 6 | 14 | 104 | 102 | 1 | 1 | 5 | 12 | 33 | 36 | 3 | -3 | 2 | 16 | 33 | 22 | 4 | 0 | 6 | 14 | 63 | 57 | 2 |
| 1 | 6 | 14 | 42 | 41 | 2 | 2 | 5 | 12 | 40 | 46 | 6 | -2 | 2 | 16 | 36 | 22 | 4 | | | | | | |

TABLE 7-continued

Observed and calculated structure factors for 2-Mbis-P

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| 0 | 6 | 14 | 21 | 8 | 4 | 1 | 3 | 15 | 43 | 57 | 6 | -2 | 2 | 16 | 153 | 147 | 3 | -1 | 3 | 18 | 29 | 23 | 4 |
| 1 | 6 | 14 | 42 | 41 | 2 | -5 | 4 | 15 | 32 | 8 | 10 | -1 | 2 | 16 | 66 | 61 | 1 | 0 | 3 | 18 | 54 | 53 | 4 |
| 2 | 6 | 14 | 106 | 102 | 1 | -4 | 4 | 15 | 41 | 33 | 8 | 0 | 2 | 16 | 57 | 58 | 5 | 2 | 3 | 18 | 49 | 57 | 3 |
| 3 | 6 | 14 | 86 | 96 | 3 | -3 | 4 | 15 | 80 | 81 | 4 | 1 | 2 | 16 | 45 | 59 | 3 | 3 | 3 | 18 | 16 | 4 | 15 |
| 4 | 6 | 14 | 54 | 36 | 5 | -2 | 4 | 15 | 93 | 94 | 3 | 2 | 2 | 16 | 40 | 46 | 3 | 4 | 4 | 18 | 27 | 29 | 18 |
| 4 | 7 | 14 | 73 | 82 | 9 | -1 | 4 | 15 | 24 | 16 | 6 | 3 | 2 | 16 | 64 | 59 | 2 | -3 | 4 | 18 | 14 | 4 | 14 |
| 3 | 7 | 14 | 32 | 34 | 7 | 0 | 4 | 15 | 90 | 92 | 1 | 4 | 2 | 16 | 25 | 16 | 7 | -2 | 4 | 18 | 52 | 45 | 3 |
| 2 | 7 | 14 | 61 | 65 | 1 | 1 | 4 | 15 | 38 | 16 | 4 | -4 | 3 | 16 | 137 | 133 | 19 | -1 | 4 | 18 | 35 | 33 | 3 |
| 1 | 7 | 14 | 176 | 179 | 1 | 2 | 4 | 15 | 96 | 94 | 5 | -3 | 3 | 16 | 36 | 20 | 6 | 0 | 4 | 18 | 48 | 47 | 2 |
| 0 | 7 | 14 | 25 | 5 | 3 | 3 | 4 | 15 | 84 | 82 | 3 | -2 | 3 | 16 | 137 | 133 | 4 | 1 | 4 | 18 | 42 | 32 | 4 |
| 1 | 7 | 14 | 181 | 179 | 2 | 4 | 4 | 15 | 25 | 33 | 2 | -1 | 3 | 16 | 24 | 17 | 2 | 2 | 4 | 18 | 58 | 45 | 3 |
| 2 | 7 | 14 | 63 | 65 | 2 | -4 | 5 | 15 | 45 | 33 | 4 | 0 | 3 | 16 | 59 | 59 | 1 | 3 | 4 | 18 | 31 | 44 | 10 |
| 3 | 7 | 14 | 29 | 34 | 10 | -3 | 5 | 15 | 60 | 64 | 4 | 1 | 3 | 16 | 40 | 46 | 3 | 4 | 5 | 18 | 43 | 35 | 3 |
| 4 | 7 | 14 | 73 | 81 | 4 | -2 | 5 | 15 | 123 | 127 | 1 | 2 | 3 | 16 | 41 | 38 | 12 | -3 | 5 | 18 | 52 | 43 | 3 |
| 4 | 8 | 14 | 31 | 26 | 7 | -1 | 5 | 15 | 46 | 48 | 2 | 3 | 3 | 16 | 58 | 55 | 3 | -2 | 5 | 18 | 53 | 48 | 2 |
| 3 | 8 | 14 | 50 | 65 | 3 | 0 | 5 | 15 | 116 | 109 | 1 | 4 | 3 | 16 | 104 | 97 | 7 | -1 | 5 | 18 | 52 | 48 | 5 |
| 2 | 8 | 14 | 72 | 69 | 2 | 1 | 5 | 15 | 50 | 48 | 2 | -4 | 4 | 16 | 80 | 75 | 2 | 0 | 5 | 18 | 53 | 49 | 3 |
| 1 | 8 | 14 | 71 | 68 | 1 | 2 | 5 | 15 | 124 | 127 | 2 | -3 | 4 | 16 | 47 | 42 | 1 | 1 | 5 | 18 | 46 | 43 | 8 |
| 0 | 8 | 14 | 102 | 107 | 1 | 3 | 5 | 15 | 59 | 64 | 3 | -2 | 4 | 16 | 81 | 75 | 2 | 2 | 5 | 18 | 36 | 35 | 7 |
| 1 | 8 | 14 | 70 | 68 | 3 | 4 | 5 | 15 | 4 | 33 | 4 | -1 | 4 | 16 | 105 | 97 | 3 | 3 | 5 | 18 | 33 | 32 | 3 |
| 2 | 8 | 14 | 71 | 69 | 4 | -4 | 6 | 15 | 43 | 36 | 7 | 0 | 4 | 16 | 54 | 54 | 4 | -2 | 6 | 18 | 65 | 66 | 4 |
| 3 | 8 | 14 | 59 | 64 | 5 | -3 | 6 | 15 | 38 | 39 | 7 | 1 | 4 | 16 | 27 | 38 | 9 | -1 | 6 | 18 | 41 | 37 | 8 |
| 4 | 8 | 14 | 4 | 26 | 2 | -2 | 6 | 15 | 76 | 73 | 1 | 2 | 4 | 16 | 41 | 38 | 4 | 0 | 6 | 18 | 8 | 3 | 2 |
| 3 | 9 | 14 | 26 | 27 | 2 | -1 | 6 | 15 | 112 | 121 | 1 | 3 | 4 | 16 | 26 | 9 | 7 | 1 | 6 | 18 | 27 | 37 | 8 |
| 2 | 9 | 14 | 37 | 11 | 25 | 0 | 6 | 15 | 58 | 57 | 2 | 4 | 4 | 16 | 78 | 79 | 13 | 2 | 6 | 18 | 62 | 66 | 2 |
| 1 | 9 | 14 | 62 | 66 | 5 | 1 | 6 | 15 | 116 | 121 | 2 | -4 | 5 | 16 | 47 | 41 | 1 | -2 | 7 | 18 | 25 | 17 | 10 |
| 0 | 9 | 14 | 60 | 59 | 2 | 2 | 6 | 15 | 70 | 73 | 2 | -3 | 5 | 16 | 84 | 88 | 2 | -1 | 7 | 18 | 45 | 38 | 3 |
| 1 | 9 | 14 | 34 | 28 | 3 | 3 | 6 | 15 | 33 | 39 | 2 | -2 | 5 | 16 | 44 | 40 | 2 | 0 | 7 | 18 | 30 | 17 | 5 |
| 2 | 9 | 14 | 57 | 59 | 2 | -3 | 7 | 15 | 17 | 36 | 8 | -1 | 5 | 16 | 78 | 79 | 2 | 1 | 7 | 18 | 42 | 45 | 15 |
| 3 | 9 | 14 | 69 | 66 | 5 | -2 | 7 | 15 | 43 | 39 | 16 | 0 | 5 | 16 | 25 | 9 | 8 | 2 | 7 | 18 | 31 | 38 | 19 |
| 3 | 10 | 14 | 16 | 27 | 4 | -1 | 7 | 15 | 33 | 31 | 2 | 1 | 5 | 16 | 45 | 38 | 10 | -2 | 8 | 18 | 36 | 38 | 3 |
| 2 | 10 | 14 | 39 | 37 | 2 | 0 | 7 | 15 | 83 | 78 | 5 | 2 | 5 | 16 | 63 | 66 | 10 | -1 | 8 | 18 | 52 | 51 | 3 |
| 1 | 10 | 14 | 37 | 37 | 3 | 1 | 7 | 15 | 38 | 29 | 8 | 3 | 5 | 16 | 17 | 23 | 2 | 0 | 8 | 18 | 61 | 61 | 3 |
| 0 | 10 | 14 | 46 | 43 | 2 | 2 | 7 | 15 | 54 | 45 | 2 | -3 | 6 | 16 | 64 | 66 | 5 | 1 | 8 | 18 | 55 | 63 | 5 |
| 1 | 10 | 14 | 72 | 75 | 2 | -2 | 8 | 15 | 44 | 29 | 5 | -2 | 6 | 16 | 77 | 80 | 9 | -1 | 9 | 18 | 47 | 51 | 13 |
| 2 | 10 | 14 | 45 | 41 | 5 | -1 | 8 | 15 | 79 | 78 | 8 | -1 | 6 | 16 | 69 | 54 | 7 | 0 | 9 | 18 | 39 | 41 | 3 |
| 2 | 11 | 14 | 33 | 37 | 2 | 0 | 8 | 15 | 6 | 31 | 2 | 0 | 6 | 16 | 21 | 14 | 1 | -1 | 10 | 18 | 16 | 12 | 6 |
| 1 | 11 | 14 | 43 | 19 | 2 | 1 | 8 | 15 | 36 | 39 | 5 | 1 | 6 | 16 | 68 | 66 | 7 | 0 | 10 | 18 | 42 | 41 | 15 |
| 0 | 11 | 14 | 27 | 37 | 1 | 2 | 8 | 15 | 35 | 32 | 6 | 2 | 6 | 16 | 9 | 23 | 6 | 0 | 11 | 18 | 15 | 6 | 9 |
| 1 | 11 | 14 | 54 | 48 | 2 | -1 | 9 | 15 | 48 | 53 | 5 | -2 | 7 | 16 | 28 | 3 | 5 | -1 | 0 | 19 | 29 | 24 | 20 |
| 1 | 12 | 14 | 51 | 53 | 4 | 0 | 9 | 15 | 28 | 37 | 4 | -1 | 7 | 16 | 50 | 41 | 4 | 0 | 0 | 19 | 37 | 25 | 3 |
| 2 | 12 | 14 | 78 | 75 | 2 | 1 | 9 | 15 | 47 | 42 | 4 | 0 | 7 | 16 | 74 | 76 | 9 | -1 | 1 | 19 | 63 | 66 | 4 |
| 1 | 10 | 14 | 53 | 53 | 4 | 2 | 9 | 15 | 120 | 122 | 2 | 1 | 7 | 16 | 96 | 97 | 7 | 0 | 1 | 19 | 48 | 54 | 12 |
| 0 | 10 | 14 | 50 | 48 | 4 | -1 | 10 | 15 | 49 | 42 | 2 | 2 | 7 | 16 | 67 | 69 | 2 | -1 | 1 | 19 | 53 | 52 | 4 |
| 1 | 11 | 14 | 32 | 30 | 2 | 0 | 10 | 15 | 40 | 37 | 4 | -1 | 0 | 17 | 58 | 61 | 3 | 0 | 1 | 19 | 17 | 8 | 12 |
| 2 | 12 | 14 | 69 | 71 | 2 | 1 | 10 | 15 | 58 | 53 | 2 | 0 | 0 | 17 | 92 | 98 | 3 | | | | | | |

TABLE 7-continued

Observed and calculated structure factors for 2-Mbis-P

| h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|------|------|-----|---|---|---|------|------|-----|---|---|---|------|------|-----|---|---|---|------|------|-----|
| 0 | 12 | 14 | 22 | 4 | 8 | -3 | 9 | 15 | 73 | 79 | 2 | 2 | 7 | 16 | 73 | 76 | 5 | 3 | 1 | 7 | 17 | 64 | 58 | 4 | 1 | 1 | 19 | 54 | 52 | 3 |
| 1 | 12 | 14 | 70 | 71 | 4 | -2 | 9 | 15 | 37 | 39 | 5 | 3 | 7 | 16 | 25 | 41 | 13 | -3 | 8 | 17 | 50 | 51 | 3 | 2 | 1 | 19 | 52 | 54 | 5 |
| 2 | 12 | 14 | 34 | 30 | 10 | -1 | 9 | 15 | 55 | 53 | 6 | 4 | 7 | 16 | 4 | 3 | 4 | -2 | 8 | 17 | 78 | 82 | 2 | 3 | 1 | 19 | 59 | 66 | 2 |
| -1 | 13 | 14 | 33 | 39 | 5 | 0 | 9 | 15 | 36 | 27 | 4 | -3 | 8 | 16 | 62 | 61 | 2 | -1 | 8 | 17 | 31 | 32 | 8 | -3 | 2 | 19 | 36 | 50 | 2 |
| 0 | 13 | 14 | 28 | 28 | 8 | 1 | 9 | 15 | 59 | 53 | 3 | -2 | 8 | 16 | 33 | 24 | 4 | 0 | 8 | 17 | 31 | 22 | 11 | -2 | 2 | 19 | 48 | 34 | 4 |
| 1 | 13 | 14 | 15 | 39 | 14 | 2 | 9 | 15 | 41 | 39 | 7 | -1 | 8 | 16 | 75 | 73 | 6 | 1 | 8 | 17 | 18 | 32 | 18 | -1 | 2 | 19 | 34 | 29 | 3 |
| -1 | 0 | 15 | 309 | 302 | 3 | -1 | 9 | 15 | 63 | 79 | 9 | 0 | 8 | 16 | 48 | 51 | 4 | -1 | 9 | 17 | 83 | 82 | 6 | 0 | 2 | 19 | 29 | 29 | 4 |
| 2 | 0 | 15 | 63 | 62 | 3 | -3 | 10 | 15 | 45 | 45 | 4 | 1 | 8 | 16 | 72 | 73 | 6 | 0 | 9 | 17 | 41 | 32 | 6 | 1 | 2 | 19 | 19 | 12 | 10 |
| 3 | 0 | 15 | 21 | 13 | 1 | -2 | 10 | 15 | 21 | 22 | 7 | 2 | 8 | 16 | 28 | 24 | 4 | 1 | 9 | 17 | 49 | 51 | 3 | 2 | 2 | 19 | 19 | 29 | 6 |
| 4 | 0 | 15 | 37 | 38 | 19 | -1 | 10 | 15 | 59 | 48 | 3 | -3 | 9 | 16 | 62 | 62 | 6 | -3 | 10 | 17 | 44 | 37 | 4 | -3 | 3 | 19 | 34 | 34 | 6 |
| -1 | 1 | 15 | 48 | 57 | 5 | 0 | 10 | 15 | 17 | 15 | 12 | -2 | 9 | 16 | 23 | 28 | 4 | -2 | 10 | 17 | 35 | 1 | 9 | -2 | 3 | 19 | 42 | 50 | 8 |
| 4 | 1 | 15 | 52 | 57 | 3 | 1 | 10 | 15 | 46 | 48 | 3 | -1 | 9 | 16 | 43 | 47 | 8 | -1 | 10 | 17 | 36 | 37 | 4 | -3 | 3 | 19 | 29 | 14 | 6 |
| 3 | 1 | 15 | 138 | 130 | 3 | 2 | 10 | 15 | 24 | 22 | 7 | 0 | 9 | 16 | 48 | 39 | 3 | 0 | 10 | 17 | 35 | 54 | 2 | -2 | 3 | 19 | 35 | 24 | 4 |
| -1 | 1 | 15 | 161 | 151 | 2 | -1 | 11 | 15 | 32 | 44 | 6 | 1 | 9 | 16 | 30 | 42 | 5 | 1 | 10 | 17 | 27 | 31 | 4 | -1 | 3 | 19 | 35 | 33 | 3 |
| 2 | 1 | 15 | 102 | 95 | 1 | 0 | 11 | 15 | 39 | 38 | 3 | -3 | 10 | 16 | 42 | 39 | 3 | -2 | 11 | 17 | 22 | 2 | 10 | 0 | 3 | 19 | 30 | 39 | 7 |
| 3 | 1 | 15 | 93 | 90 | 6 | 1 | 11 | 15 | 33 | 20 | 4 | -2 | 10 | 16 | 40 | 47 | 3 | -1 | 11 | 17 | 18 | 21 | 12 | 1 | 3 | 19 | 41 | 24 | 4 |
| -1 | 1 | 15 | 101 | 95 | 2 | -1 | 0 | 19 | 22 | 21 | 2 | -1 | 10 | 16 | 26 | 28 | 4 | 0 | 11 | 17 | 27 | 7 | 6 | -3 | 4 | 19 | 24 | 19 | 10 |
| 0 | 1 | 15 | 33 | 54 | 2 | 2 | 0 | 19 | 2 | 15 | 4 | 0 | 10 | 16 | 34 | 10 | 13 | -3 | 0 | 20 | 21 | 25 | 6 | -2 | 4 | 19 | 36 | 32 | 18 |
| 1 | 1 | 15 | 33 | 31 | 4 | -1 | 0 | 19 | 2 | 2 | 3 | -1 | 11 | 16 | 37 | 41 | 7 | -2 | 0 | 20 | 21 | 18 | 6 | -1 | 4 | 19 | 39 | 37 | 6 |
| 4 | 4 | 15 | 50 | 51 | 3 | 0 | 0 | 19 | 54 | 31 | 4 | 0 | 11 | 16 | 71 | 47 | 3 | -1 | 0 | 20 | 30 | 18 | 8 | 0 | 4 | 19 | 37 | 17 | 6 |
| -1 | 1 | 15 | 20 | 31 | 10 | -1 | 0 | 19 | 20 | 31 | 4 | -1 | 0 | 17 | 46 | 58 | 6 | 0 | 0 | 20 | 28 | 26 | 5 | 1 | 4 | 19 | 25 | 17 | 7 |
| 2 | 4 | 15 | 46 | 54 | 5 | 1 | 0 | 19 | 46 | 54 | 7 | 0 | 0 | 17 | 58 | 58 | 4 | 1 | 0 | 20 | 33 | 26 | 11 | 2 | 4 | 19 | 33 | 37 | 11 |
| -1 | 1 | 15 | 38 | 27 | 7 | -1 | 1 | 19 | 20 | 10 | 9 | 1 | 0 | 17 | 39 | 37 | 4 | -3 | 1 | 20 | 21 | 2 | 15 | -3 | 5 | 19 | 14 | 19 | 14 |
| 2 | 5 | 15 | 20 | 18 | 11 | 0 | 1 | 19 | 33 | 28 | 10 | -3 | 1 | 17 | 29 | 33 | 9 | -2 | 1 | 20 | 13 | 7 | 12 | -2 | 5 | 19 | 41 | 43 | 14 |
| 5 | 5 | 15 | 19 | 28 | 6 | 1 | 1 | 19 | 28 | 29 | 6 | -2 | 1 | 17 | 42 | 33 | 4 | -1 | 1 | 20 | 45 | 43 | 4 | -1 | 5 | 19 | 29 | 15 | 9 |
| 1 | 5 | 15 | 29 | 29 | 18 | -1 | 2 | 19 | 19 | 20 | 6 | -1 | 1 | 17 | 39 | 37 | 2 | 0 | 1 | 20 | 33 | 28 | 7 | 1 | 5 | 19 | 10 | 14 | 4 |
| 2 | 5 | 15 | 19 | 29 | 6 | 0 | 2 | 19 | 29 | 29 | 6 | 0 | 1 | 17 | 36 | 36 | 3 | 1 | 1 | 20 | 61 | 69 | 6 | -2 | 6 | 19 | 24 | 49 | 5 |
| -1 | 1 | 15 | 29 | 20 | 6 | 1 | 2 | 19 | 19 | 20 | 18 | 1 | 1 | 17 | 40 | 47 | 3 | -3 | 2 | 20 | 50 | 51 | 3 | -1 | 6 | 19 | 44 | 35 | 6 |
| 0 | 6 | 15 | 31 | 12 | 6 | -1 | 3 | 19 | 22 | 15 | 8 | -3 | 2 | 17 | 53 | 47 | 4 | -2 | 2 | 20 | 21 | 19 | 6 | 0 | 6 | 19 | 39 | 31 | 6 |
| 1 | 6 | 15 | 22 | 20 | 15 | 0 | 3 | 19 | 34 | 15 | 10 | -2 | 2 | 17 | 31 | 30 | 9 | -1 | 2 | 20 | 55 | 51 | 3 | -2 | 7 | 19 | 27 | 13 | 6 |
| 2 | 6 | 15 | 34 | 15 | 15 | 1 | 3 | 19 | 16 | 23 | 15 | -1 | 2 | 17 | 57 | 47 | 4 | 0 | 2 | 20 | 27 | 65 | 4 | -1 | 7 | 19 | 21 | 31 | 6 |
| -1 | 7 | 15 | 27 | 23 | 5 | -1 | 4 | 19 | 27 | 20 | 5 | 0 | 2 | 17 | 26 | 34 | 9 | 1 | 2 | 20 | 44 | 32 | 7 | 0 | 7 | 19 | 21 | 31 | 6 |
| 0 | 7 | 15 | 32 | 23 | 5 | | | | | | | 1 | 2 | 17 | 30 | 25 | 5 | 2 | 2 | 20 | 28 | 24 | 3 | 2 | 7 | 19 | 35 | 37 | 6 |
| | | | | | | | | | | | | 2 | 2 | 17 | 18 | 18 | 17 | -3 | 3 | 20 | 45 | 47 | 5 | | | | | | | |

Synthesis of 2MBP

EXAMPLE 3

The preparation of 2MBP having the basic structure I can be accomplished by a common general method, i.e. the condensation of a bicyclic Windaus-Grundmann type ketone II with the allylic phosphine oxide III to the corresponding 2-methylene-19-nor-vitamin D analog IV followed by deprotection at C-1 and C-3 in the latter compound IV to obtain compound I, i.e. 2MBP.

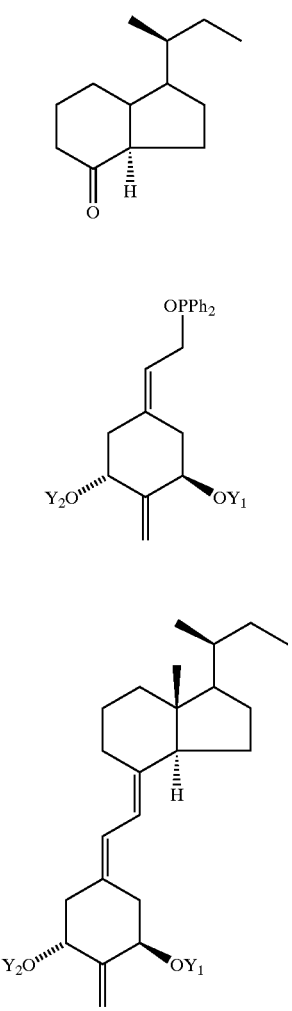

In the structures II, III, and IV groups $Y_1$ and $Y_2$ are hydroxy-protecting groups, it being also understood that any functionalities that might be sensitive, or that interfere with the condensation reaction, be suitably protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

Hydrindanones of the general structure II art known, or can be prepared by known methods.

For the preparation of the required phosphine oxides of general structure III, a synthetic route has been developed starting from a methyl quinicate derivative which is easily obtained from commercial (1R,3R,4S,5R)-(−)-quinic acid as described by Perlman et al., Tetrahedron Lett. 32, 7663 (1991) and DeLuca et al., U.S. Pat. No. 5,086,191.

The overall process of the synthesis of compound I is illustrated and described more completely in U.S. Pat. No. 5,843,928 entitled "2-Alkylidene-19-Nor-Vitamin D Compounds" and in application Ser. No. 09/878,438 filed Jun. 11, 2001 entitled "1α-Hydroxy-2-Methylene-19-Nor-Homopregnacalciferol and its Uses" the specifications of which are specifically incorporated herein by reference.

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description of the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl", "aminoalkyl", "halogenalkyl", "alkoxyalkyl", "aryloxyalkyl", and "fluoroalkyl" refer to an alkyl radical substituted by one or more hydroxy, deuterium, amino, halogen, alkoxy, aryloxy, or fluoro group respectively. A "halogen" group includes any of the five elements fluorine, chlorine, bromine, iodine and astatine that form a part of group VIIA of the periodic table.

Referring now to Schemes I–III, there are illustrated three different methods of synthesizing 2MBP starting with vitamin $D_2$. The first five steps are identical (shown in Scheme I) for each synthesis to obtain the protected 20(S)-aldehyde. Thereafter, in Schemes I and II the aldehyde is converted to a protected 20(S)-alcohol which in turn has its side chain converted to bis-homo in two different ways (Scheme I versus Scheme II). In contrast, Scheme III illustrates a direct conversion of the protected 20(S)aldehyde to the bis-homo side chain.

SCHEME I
Synthesis of 1α-hydroxy-2-methylene-19-nor-bishomopregnacalciferol
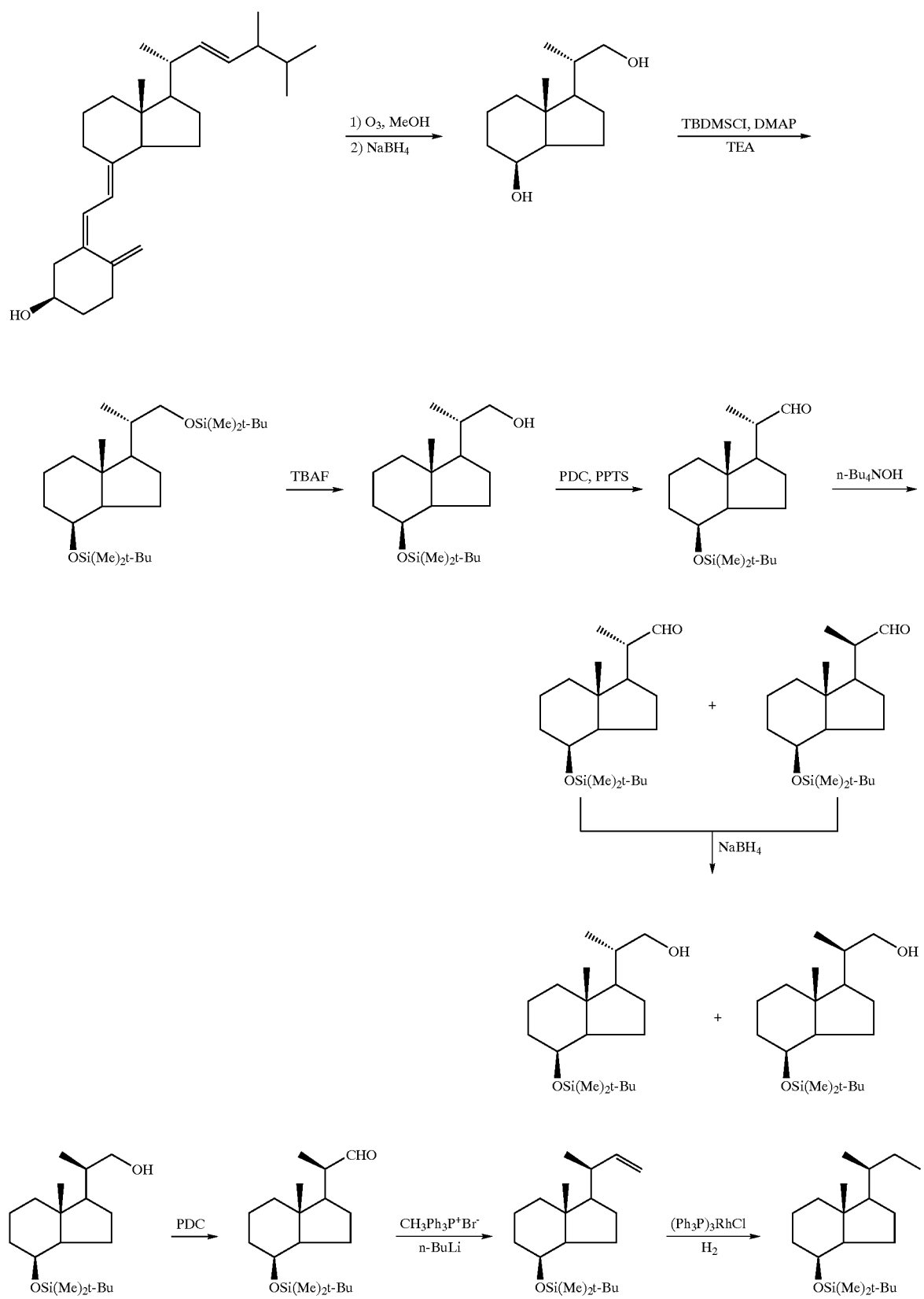

37 38
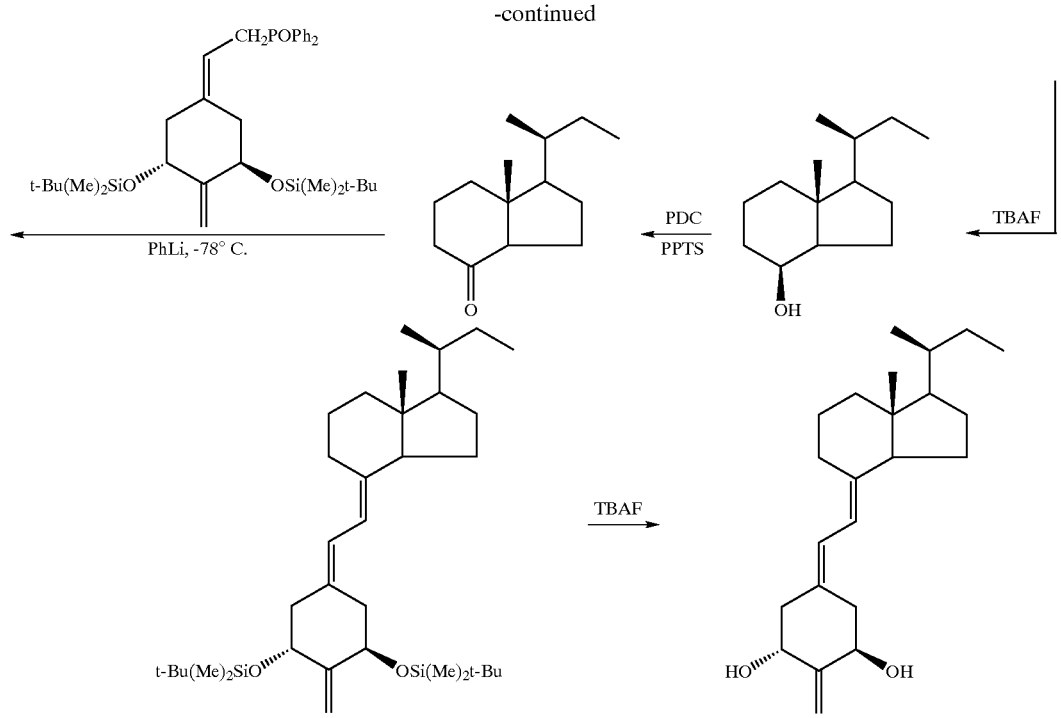
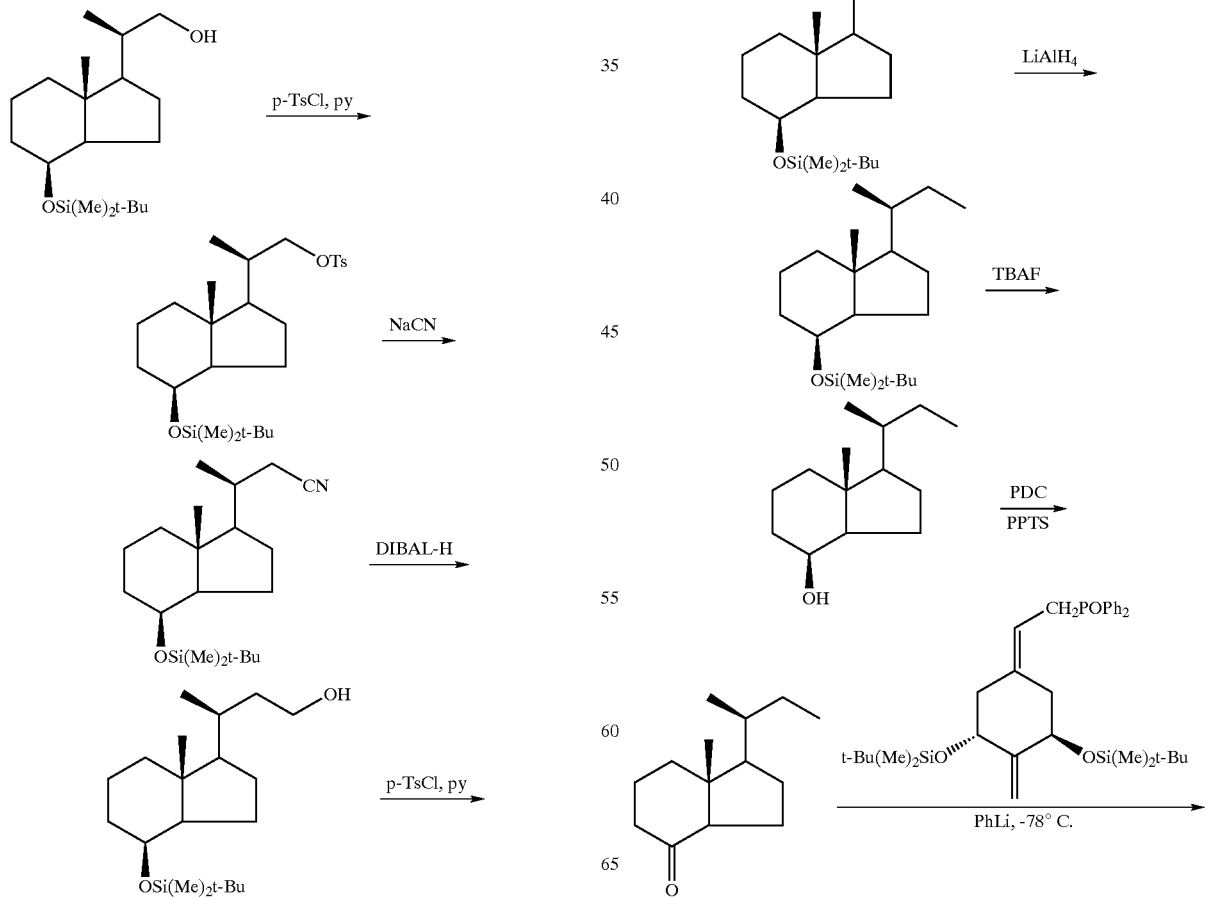
SCHEME II

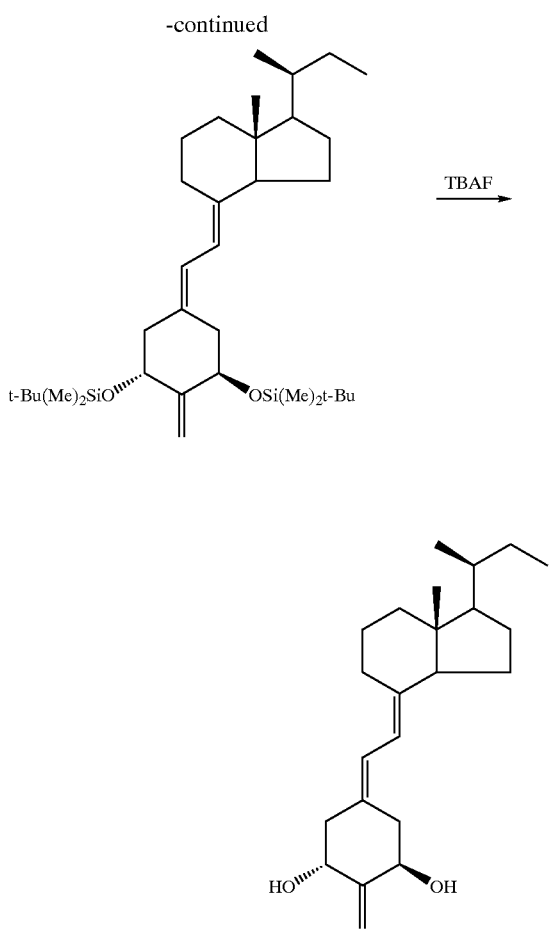
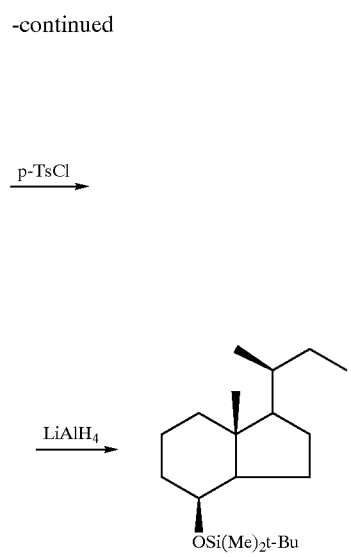
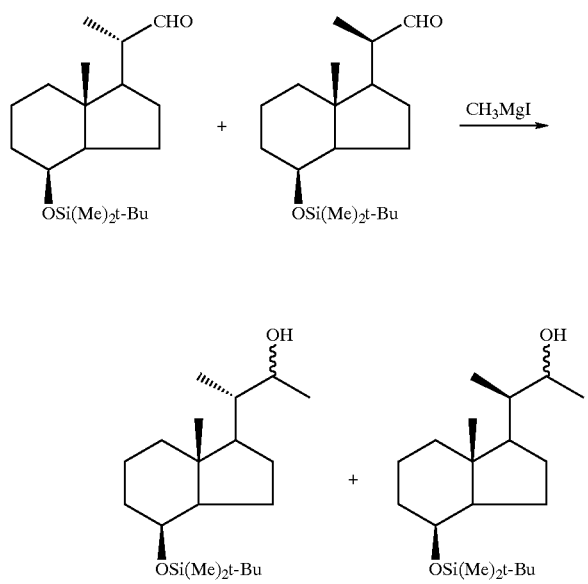

We claim:

1. (20S)-1α-hydroxy-2-methylene-19-nor-bishomopregnacalciferol in crystalline form.

2. The crystalline form of (20S)-1α-hydroxy-2-methylene-19-nor-bishomopregnacalciferol having molecular packing arrangement defined by orthorhombic space group P2(1)2(1)2(1) and unit cell dimensions a=6.6A°, b=15.5A°, c=20.1A°, α=90°, β=90° and γ=90°.

3. A three dimensional structure for (20S)-1α-hydroxy-2-methylene-19-nor-bishomopregnacalciferol as defined by the molecular packing arrangement set forth in claim 2.

4. A method of purifying (20S)-1α-hydroxy-2-methylene-19-nor-bishomopregnacalciferol, comprising the steps of:
(a) boiling a solvent selected from the group consisting of acetone, ethyl acetate, isopropanol, chloroform, dichloromethane and diethyl ether under inert atmosphere;
(b) dissolving a product containing (20S)-1α-hydroxy-2-methylene-19-nor-bishomopregnacalciferol to be purified in said solvent;
(c) cooling said solvent and dissolved product below ambient temperature for a sufficient amount of time to form a precipitate of (20S)-1α-hydroxy-2-methylene-19-nor-bishomopregnacalciferol crystals, and
(d) separating the (20S)-1α-hydroxy-2-methylene-19-nor-bishomopregnacalciferol crystals from the solvent.

5. The method of claim 4 including the further step of allowing said solvent and dissolved product to cool to ambient temperature prior to cooling below ambient temperature.

6. The method of claim 4 wherein said inert atmosphere is an argon atmosphere.

7. The method of claim 4 wherein said solvent and dissolved product is cooled to between about 35° F. to about 45° F.

8. The method of claim 4 wherein the step of separating comprises filtering the solvent and precipitate to obtain the crystals.

9. The method of claim 4 including a further step (e) comprising repeating steps (a) through (d) using the recovered crystals from step (d) as the product of step (b).

* * * * *

/

(12) EX PARTE REEXAMINATION CERTIFICATE (7593rd)
United States Patent
DeLuca et al.

(10) Number: US 6,835,723 C1
(45) Certificate Issued: Jul. 6, 2010

(54) 2-METHYLENE-19-NOR-20(S)-1α-HYDROXY-BIS-HOMO-PREGNACALCIFEROL IN CRYSTALLINE FORM

(75) Inventors: Hector F. DeLuca, Deerfield, WI (US); James B. Thoden, Madison, WI (US); Hazel M. Holden, Fitchburg, WI (US); Margaret Clagett-Dame, Deerfield, WI (US); Sumithra Gowlugari, Madison, WI (US); Pawel Grzywacz, Madison, WI (US)

(73) Assignee: Wisconsin Alumni Research Foundation, Madison, WI (US)

Reexamination Request:
No. 90/010,158, May 6, 2008

Reexamination Certificate for:
Patent No.: 6,835,723
Issued: Dec. 28, 2004
Appl. No.: 10/317,467
Filed: Dec. 12, 2002

Related U.S. Application Data
(60) Provisional application No. 60/341,138, filed on Dec. 13, 2001.

(51) Int. Cl.
*A61K 31/59* (2006.01)
*C07C 401/00* (2006.01)

(52) U.S. Cl. .................. 514/167; 514/653
(58) Field of Classification Search .................. None
See application file for complete search history.

(56) References Cited

U.S. PATENT DOCUMENTS

| | | | |
|---|---|---|---|
| 4,666,634 A | 5/1987 | Miyamoto et al. | 260/397.2 |
| 4,800,198 A | 1/1989 | DeLuca et al. | 514/167 |
| 5,089,641 A | 2/1992 | DeLuca et al. | 552/653 |
| 5,536,713 A | 7/1996 | Deluca et al. | 514/167 |
| 5,578,587 A | 11/1996 | DeLuca et al. | 514/167 |
| 5,587,497 A | 12/1996 | DeLuca et al. | 552/653 |
| 5,843,928 A * | 12/1998 | Deluca et al. | 514/167 |
| 5,936,133 A | 8/1999 | Deluca et al. | 568/828 |
| 5,945,410 A | 8/1999 | DeLuca et al. | 514/167 |
| 6,627,622 B2 | 9/2003 | DeLuca et al. | |

FOREIGN PATENT DOCUMENTS
WO  WO96/01811  1/1996

OTHER PUBLICATIONS

Brown et al, "New Active Analogues of Vitamin D with Low Calcemic Activity" Kidney International, vol. 38, Suppl. 29 (1990) pp. S–22–S–27.

Hareau et al, "Asymmetric Synthesis of 1α,25–Dihydroxyvitamin $D_3$ A–Ring Precursor Starting with 5–Tert–Butyldimethylsiloxy–2–Cyclohexenone" Tetrahedron Letters, 41 (2000) pp. 2385–2388.

Sicinski et al, "New 1α,25–Dihydroxy–19–Norvitamin $D_3$ Compounds of High Biological Activity: Synthesis and Biological Evaluation of 2–Hydroxymethyl, 2–Methyl, and 2–Methylene Analogues" J. Med. Chem., 41 (1998) pp. 4662–4674.

Posner et al, "2–Fluoroalkyl A–Ring Analogs of 1,25–Dihydroxyvitamin $D_3$–Sterocontrolled Total Synthesis via Intramolecular and Intermolecular Diels–Alder Cycloadditions. Preliminary Biological Testing", J. Org. Chem. 60, pp. 4617–4626.

\* cited by examiner

*Primary Examiner*—Evelyn Huang

(57) ABSTRACT

A method of purifying 2-methylene-19-nor-20(S)-1α-hydroxy-bis-homo-pregnacaciferol to obtain 2-methylene-19-nor-20(S)-1α-hydroxy-bis-homo-pregnacalciferol in crystalline form. The method includes the steps of boiling a solvent such as acetone under inert atmosphere, dissolving a product containing 2-methylene-19-nor-20(S)-1α-hydroxy-bis-homo-pregnacalciferol to be purified in the solvent, cooling the solvent and dissolved product below ambient temperature for a sufficient amount of time to form a precipitate of 2-methylene-19-nor-20(S)-1α-hydroxy-bis-homo-pregnacalciferol crystals, and recovering the 2-methylene-19-nor-20(S)-1α-hydroxy-bis-homo-pregnacalciferol crystals.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 2-9 is confirmed.

Claim 1 is cancelled.

\* \* \* \* \*